United States Patent
Youngquist et al.

(10) Patent No.: US 6,723,717 B1
(45) Date of Patent: Apr. 20, 2004

(54) SULFUR-CONTAINING THYROXANE DERIVATIVES AND THEIR USE AS HAIR GROWTH PROMOTORS

(75) Inventors: Robert Scott Youngquist, Mason, OH (US); John McMillan McIver, Cincinnati, OH (US)

(73) Assignee: The University of Texas Southwestern Medical Center, Dallas, TX (US)

( * ) Notice: Subject to any disclaimer, the term of this patent is extended or adjusted under 35 U.S.C. 154(b) by 0 days.

(21) Appl. No.: 09/980,404
(22) PCT Filed: Mar. 1, 2000
(86) PCT No.: PCT/US00/05252
§ 371 (c)(1), (2), (4) Date: Nov. 30, 2001
(87) PCT Pub. No.: WO00/73265
PCT Pub. Date: Dec. 7, 2000

Related U.S. Application Data

(60) Provisional application No. 60/137,063, filed on Jun. 1, 1999.

(51) Int. Cl.$^7$ .............................................. A61K 31/535
(52) U.S. Cl. .................... 514/231.2; 514/183; 514/613; 564/215; 564/218; 564/336; 544/158; 548/570; 568/28; 568/38; 568/58
(58) Field of Search ................................ 564/123, 161, 564/192, 204, 207, 215, 218, 222, 305, 336; 568/27, 28, 38, 58; 544/106, 158; 548/400, 570

(56) References Cited

U.S. PATENT DOCUMENTS

| | | |
|---|---|---|
| 3,530,146 A | 9/1970 | Newman et al. |
| 3,616,237 A | 10/1971 | Newman et al. |
| 4,323,691 A | 4/1982 | Ours et al. |
| 4,425,404 A | 1/1984 | Suzuki et al. |
| 4,683,241 A | 7/1987 | Miyano et al. |
| 4,711,855 A | 12/1987 | Feinberg |
| 5,061,798 A | 10/1991 | Emmett et al. |
| 5,284,971 A | 2/1994 | Walker et al. |
| 5,401,772 A | 3/1995 | Yokoyama |
| 5,569,674 A | 10/1996 | Yokoyama |
| 5,580,722 A | 12/1996 | Liechtfried et al. |
| 5,654,468 A | 8/1997 | Yokoyama |
| 5,773,663 A | 6/1998 | Rehing et al. |
| 5,807,820 A | 9/1998 | Elias |
| 5,883,294 A | 3/1999 | Scanlan et al. |
| 6,174,925 B1 | 1/2001 | Bailey et al. |
| 6,221,911 B1 | 4/2001 | Lavin et al. |

FOREIGN PATENT DOCUMENTS

| | | | |
|---|---|---|---|
| EP | 123528 | * | 2/1984 |
| EP | 0749752 | | 12/1996 |
| WO | 9625943 | * | 8/1996 |
| WO | WO0000468 | | 1/2000 |

OTHER PUBLICATIONS

CA:68:49240 abs of Bulletin of the Chemical Society of Japan by Oae et al 40(4) pp 951–8 1967.*
CA:121:133683 abs of WO9408956 Apr. 1994.*
CA:117:127091 abs of Theochem by De Benedetti P.G. 88 pp 231–48 1992.*
CA:55:48487 abs of J Karnatak Univ by Nargund et al 4 pp 56–70 1960.*
CA:59:48033 abs of Compt. Rend. by Quelet et al 257(1) pp 1269–71 1963.*
CA:138:4422 abs of WO2002094770 Nov. 2002.*
CA:96:19855 abs of EP 35712 Sep. 1981.*
"Hair Growth–Stimulating Effects of Cyclosporin A and Fk506, Potent Immunosuppressants", Journal of Dermatological Service, vol. 7 (suppl.), pp. S47–S54 (1994).
"Hair Growth Modulation by Topical Immunophilin Ligands", American Journal of Pathology, vol. 150, No. 4, pp. 1433–1441 (Apr. 1997).
Hair Growth Control by Immunosuppression:, Archives of Dermatological Research, vol. 288, No. 7, pp. 408–410 (1996).
Cyclosporin A, PSC 833 and FK 506, but not Cyclosporin H and Rapamycin, Induce Anagen and Inhibit Catagen In Murine Skin, The Journal of Investigative Dermatology, vol. 101, No. 3, p. 420 (1993).
"Cyclosporin A, FK 506 and Related Drugs as Tools for Hair Research", Archives of Dermatological Research, vol. 285, Nos. 1–2, p. 80 (1993).

(List continued on next page.)

*Primary Examiner*—Jean F. Vollano
(74) *Attorney, Agent, or Firm*—Michael Best & Friedrich LLP

(57) ABSTRACT

The present disclosure describes novel compounds of formula (A), wherein $R_1$–$R_{12}$, X and Y have the meanings given in the specification and compositions containing them which are particularly useful for treating hair loss in mammals, including arresting and/or reversing hair loss and promoting hair growth. The compounds described herein are cardiac-sparing.

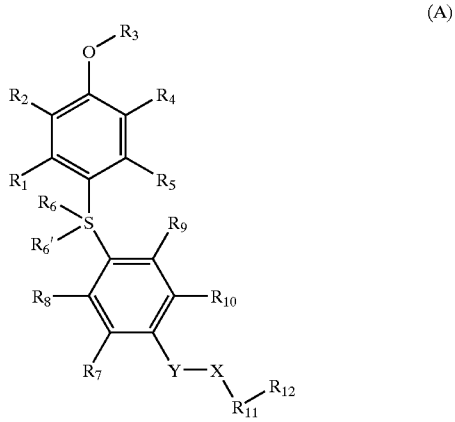

8 Claims, No Drawings

OTHER PUBLICATIONS

"Cyclosporins—New Analogues by Precursor Directed Biosyntheses", The Journal of Antibiotics, vol. 42, No. 4, pp. 591–597 (1989).

N Yokoyama: "Synthesis and structure–activity relationships of oxamic acid and acetic acid derivatives related to L–thronine", Journal of Medicinal Chemistry, US, American Chemical Society, Washington, vol. 38, No. 4, 1995, pp. 695–707.

Vinod. K. Sharma et al: "Evaluation of thyroid function in North Indians with alopecia areta: Response to intravenous injection of 100microgram thyrotropin releasing hormone (TRH)", vol. 26, No. 6, pp. 339–342 (1999).

Berman, et al., Peripheral Effects of L–Thyroxine on Hair Growth and Coloration in Cattle, J. Endocrin 20:288–292 (1960).

Gunaratnam, The Journal of Small Animal Practice, (1986), pp. 17–29, vol. 27, No. 1.

Hale, et al., The Journal of Experimental Zoology, (1975), pp. 49–62, 191.

* cited by examiner

SULFUR-CONTAINING THYROXANE DERIVATIVES AND THEIR USE AS HAIR GROWTH PROMOTORS

This application claims the benefit of provisional application No. 60/137/063, filed Jun. 1, 1994.

FIELD OF THE INVENTION

The present invention relates to methods for treating hair loss is arresting and/or reversing hair loss and promoting hair growth.

BACKGROUND OF THE INVENTION

Hair loss is a common problem which occurs, for example, through natural processes or is often chemically promoted through the use of certain therapeutic drugs designed to alleviate conditions such as cancer. Often such hair loss is accompanied by lack of hair regrowth which causes partial or full baldness.

As is well-known in the art, hair growth occurs by a cycle of activity which involves alternating periods of growth and rest. This cycle is often divided into three main stages which are known as anagen, catagen, and telogen. Anagen is the growth phase of the cycle and may be characterized by penetration of the hair follicle deep into the dermis with rapid proliferation of cells which are differentiating to form hair. The next phase is catagen, which is a transitional stage marked by the cessation of cell division, and during which the hair follicle regresses through the dermis and hair growth is ceased. The next phase, telogen, is often characterized as the resting stage during which the regressed follicle contains a germ with tightly packed dermal papilla cells. At telogen, the initiation of a new anagen phase is caused by rapid cell proliferation in the germ, expansion of the dermal papilla, and elaboration of basement membrane components. Wherein hair growth ceases, most of the hair follicles reside in telogen and anagen is not engaged, thus causing the onset of full or partial baldness.

There have been many attempts in the literature to invoke the regrowth of hair by, for example, the promotion or prolongation of anagen. Currently, there are two drugs approved by the United States Food and Drug Administration for the treatment of male pattern baldness: topical minoxidil (marketed as Rogaine® by Pharmacia & Upjohn), and oral finasteride (marketed as Propecia® by Merck & Co., Inc.). For several reasons, however, including safety concerns and/or lack of efficacy, the search for efficacious hair growth inducers is ongoing.

Interestingly, it is known that the thyroid hormone known as thyroxine ("T4") converts to thyronine ("T3") in human skin by deiodinase 1, a selenoprotein. Selenium deficiency causes a decrease in T3 levels due to a decrease in deiodinase I activity; this reduction in T3 levels is strongly associated with hair loss. Consistent with this observation, hair growth is a reported side effect of administration of T4. See, e.g., Berman. "Peripheral Effects of L-Thyroxine on Hair Growth and Coloration in Cattle ". *Journal of Endocrinology*, Vol. 20, pp. 282–292 (1960): and Gunaratnam. "The Effects of Thyroxine on Hair Growth in the Dog", *J. Small Anim. Pract.*, Vol. 27, pp. 17–29 (1986). Furthermore, T3 and T4 have been the subject of several patent publications relating to treatment of hair loss. See, e.g., Fischer et al., DE 1,617,477, published Jan. 8, 1970; Mortimer, GB 2,138,286, published Oct. 24, 1984; and Lindenbaum, WO 96/25943, assigned to Life Medical Sciences. Inc., published Aug. 29, 1996.

Unfortunately, however, administration of T3 and/or T4 to treat hair loss is not practicable because these thyroid hormones are also known to induce significant cardiotoxicity. See, e.g., Walker et al., U.S. Pat. No. 5,284,971, assigned to Syntex, issued Feb. 8, 1994 and Emmett et al., U.S. Pat. No. 5,061,798, assigned to Smith Kline & French Laboratories, issued Oct. 29, 1991. Surprisingly, the present inventors have discovered compounds which strongly initiate hair growth without inducing cardiotoxicity. Consistent with this discovery, but without intending to be limited by theory, the present inventors have surprisingly discovered that the preferred compounds of the present invention interact strongly with hair-selective thyroid hormone receptors but interact less strongly, or not at all, with heart-selective hormone receptors. These unique properties are, of course, not shared with T3 and/or T4. Accordingly, the compounds and compositions herein are useful for treating hair loss, including arresting and/or reversing hair loss and promoting hair growth.

SUMMARY OF THE INVENTION

The present invention relates to compounds and compositions which are particularly useful for treating hair loss in mammals, including arresting and/or reversing hair loss and promoting hair growth.

The compounds of the present invention have the structure:

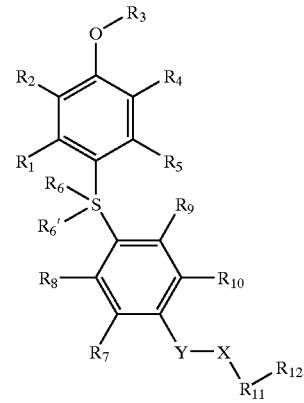

and pharmaceutically acceptable salts, hydrates, and biohydrolyzable amides, esters, and imides thereof, wherein $R_1$, $R_2$, $R_3$, $R_4$, $R_5$, $R_6$, $R_6'$, $R_7$, $R_8$, $R_9$, $R_{10}$, Y, X, $R_{11}$, and $R_{12}$ are defined herein.

DETAILED DESCRIPTION OF THE INVENTION

The present, invention relates to compounds and compositions which are particularly useful for treating hair loss in mammals, including arresting and/or reversing hair loss and promoting hair growth.

In addition to discovering that the present compounds are useful for treating hair loss, the present inventors have also surprisingly discovered that the preferred compounds of the present invention are cardiac-sparing.

Publications and patents are referred to throughout this disclosure. All references cited herein are hereby incorporated by reference.

All percentages, ratios, and proportions used herein are by weight unless otherwise specified.

In the description of the invention various embodiments and/or individual features are disclosed. As will be apparent to the ordinarily skilled practitioner all combinations of such embodiments and features are possible and can result in preferred executions of the invention.

As used herein, wherein any variable, moiety, group, or the like occurs more than one time in any variable or structure, its definition at each occurrence is independent of its definition at every other occurrence.

Definition and Usage of Terms

The following is a list of definitions for terms used herein:

As used herein "salt" is a cationic salt formed at any acidic (e.g., carboxyl) group, or an anionic salt formed at any basic (e.g., amino) group. Many such salts are known in the art. Preferred cationic salts include the alkali metal salts (such as, for example, sodium and potassium), alkaline earth metal salts (such as, for example, magnesium and calcium), and organic salts. Preferred anionic salts include the halides (such as, for example, chloride salts). Such acceptable salts must, when administered, be appropriate for mammalian use.

As used herein, "alkenyl" is an unsubstituted or substituted hydrocarbon chain radical having from 2 to about 15 carbon atoms; preferably from 2 to about 10 carbon atoms; more preferably from 2 to about 8 carbon atoms, and most preferably from about 2 to about 6 carbon atoms. Alkenyls have at least one olefinic double bond. Non-limiting examples of alkenyls include vinyl, allyl, and butenyl.

As used herein, "alkoxy" is an oxygen radical having an alkyl, alkenyl, or alkynyl, preferably an alkyl or alkenyl, and most preferably an alkyl substituent. Examples of alkoxy radicals include —O-alkyl and —O-alkenyl. An alkoxy radical may be substituted or unsubstituted.

As used herein, "aryloxy" is an oxygen radical having an aryl substituent. An aryloxy radical may be substituted or unsubstituted.

As used herein, "alkyl" is an unsubstituted or substituted saturated hydrocarbon chain radical having from 1 to about 15 carbon atoms; preferably from 1 to about 10 carbon atoms: more preferably from 1 to about 6 carbon atoms; and most preferably from 1 to about 4 carbon atoms. Preferred alkyls include, for example, methyl, ethyl, propyl, isopropyl, and butyl.

As used herein, "alkylene" refers to an alkyl, alkenyl, or alkynyl which is a diradical. For example, "methylene" is —CH$_2$—. Alkylenes may be substituted or unsubstituted.

As used herein, "alkynyl" is an unsubstituted or substituted hydrocarbon chain radical having from 2 to about 15 carbon atoms; preferably from 2 to about 10 carbon atoms; more preferably from 2 to about 8 carbon atoms, and most preferably from about 2 to about 6 carbon atoms. Alkynyls have at least one triple bond.

As used herein, "aryl" is an aromatic ring radical which is either carbocyclic or heterocyclic. Preferred aryl groups include, for example, phenyl, benzyl, tolyl, xylyl, cumenyl, napthyl, biphenyl, thienyl, furyl, pyrrolyl, pyridinyl, pyrazinyl, thiazolyl, pyrimidinyl, quinolinyl, triazolyl, tetrazolyl, benzothiazolyl, benzofuryl, indolyl, indenyl, azulenyl, fluorenyl, anthracenyl, oxazolyl, isoxazolyl, isotriazolyl, imidazolyl, pyraxolyl, oxadiazolyl, indolizinyl, indolyl, isoindolyl, purinyl, quinolizinyl, quinolinyl, isoquinolinyl, cinnolinyl, and the like. Aryls may be substituted or unsubstituted.

As used herein, "arylalkenyl" is an alkenyl radical substituted with an aryl group or an aryl radical substituted with an alkenyl group. Arylalkenyls may be substituted or unsubstituted.

As used herein, "arylalkyl" is an alkyl radical substituted with an aryl group or an aryl radical substituted with an alkyl group. Preferred arylalkyl groups include benzyl, phenylethyl, and phenylpropyl. Arylalkyls may be substituted or unsubstituted.

As used herein, "biohydrolyzable amides" are amides of the compounds of the present invention which do not interfere with the activity of the compound, or that are readily converted in vivo by a mammalian subject to yield an active compound.

As used herein, "biohydrolyzable esters" are esters of the compounds of the present invention which do not interfere with the activity of the compound, or that are readily converted in vivo by a mammalian subject to yield an active compound.

As used herein, "biohydrolyzable imides" are imides of the compounds of the present invention which do not interfere with the activity of the compound, or that are readily converted in vivo by a mammalian subject to yield an active compound.

As used herein, "carbocyclic ring", "carbocycle", or the like is a hydrocarbon ring radical. Carbocyclic rings are monocyclic or are fused, bridged, or spiro polycyclic rings. Unless otherwise specified, monocyclic rings contain from 3 to about 9 atoms, preferably from about 4 to about 7 atoms, and most preferably 5 or 6 atoms. Polycyclic rings contain from about 7 to about 17 atoms, preferably from about 7 to about 14 atoms, and most preferably 9 or 10 atoms. Carbocyclic rings (carbocycles) may be substituted or unsubstituted.

As used herein, "cycloalkyl" is a saturated carbocyclic or heterocyclic ring radical. Preferred cycloalkyl groups include, for example, cyclobutyl, cyclopentyl, and cyclohexyl. Cycloalkyls may be substituted or unsubstituted.

As used herein, "cycloalkenyl" is an unsaturated carbocyclic or heterocyclic ring radical having at least one double bond. Cycloalkenyls may be substituted or unsubstituted.

As used herein, preferred "halogens" (or "halos" or the like) are bromine, chlorine, iodine, and fluorine, more preferably, bromine, chlorine, and iodine, even more preferably bromine and chlorine, and most preferably chlorine.

As used herein, "heteroalkenyl" is an alkenyl radical comprised of carbon atoms and one or more heteroatoms wherein the heteroatoms are selected from the group consisting of oxygen, sulfur, nitrogen, and phosphorous, more preferably, oxygen, sulfur, and nitrogen. Heteroalkenyls may be substituted or unsubstituted.

As used herein, "heteroalkyl" is an alkyl radical comprised of carbon atoms and one or more heteroatoms wherein the heteroatoms are selected from the croup consisting of oxygen, sulfur, nitrogen, and phosphorous, more preferably, oxygen, sulfur, and nitrogen. Heteroalkyls may be substituted or unsubstituted.

As used herein, "heteroalkynyl" is an alkynyl radical comprised of carbon atoms and one or more heteroatoms wherein the heteroatoms are selected from the group consisting of oxygen, sulfur, nitrogen, and phosphorous, more preferably, oxygen, sulfur, and nitrogen. Heteroalkynyls may be substituted or unsubstituted.

As used herein, "heteroaryl" is an aryl radical comprised of carbon atoms and one or more heteroatoms wherein the heteroatoms are selected from the group consisting of oxygen, sulfur, nitrogen, and phosphorous, more preferably, oxygen, sulfur, and nitrogen. Heteroaryls may be substituted or unsubstituted.

As used herein, "heteroarylalkenyl" is an arylalkenyl radical wherein the aryl group and/or the alkenyl group is comprised of carbon atoms and one or more heteroatoms wherein the heteroatoms are selected from the group consisting of oxygen, sulfur, nitrogen, and phosphorous, more preferably, oxygen, sulfur, and nitrogen. Heteroarylalkenyls may be substituted or unsubstituted.

As used herein, "heteroarylalkyl" is an arylalkyl radical wherein the aryl group and/or the alkyl group is comprised of carbon atoms and one or more heteroatoms wherein the heteroatoms are selected from the group consisting of oxygen, sulfur, nitrogen, and phosphorous, more preferably, oxygen, sulfur, and nitrogen. Heteroarylalkyls may be substituted or unsubstituted.

As used herein, "heterocyclic ring", "heterocycle", or the like is a ring radical comprised of carbon atoms and one or more heteroatoms in the ring wherein the heteroatoms are selected from the group consisting of oxygen, sulfur, nitrogen, and phosphorous, more preferably, oxygen, sulfur, and nitrogen. Heterocycles are monocyclic or are fused, bridged, or Spiro polycyclic rings. Unless otherwise specified, monocycles contain from 3 to about 9 atoms, preferably from about 4 to about 7 atoms, and most preferably 5 or 6 atoms. Polycycles contain from about 7 to about 17 atoms, preferably from about 7 to about 14 atoms, and most preferably 9 or 10 atoms. Heterocyclic rings (heterocycles) may be substituted or unsubstituted.

As used herein, "heterocycloalkyl" is a cycloalkyl having at least one heteroatom in the ring. Heterocycloalkyls may be substituted or unsubstituted.

As used herein, "heterocycloalkenyl" is a cycloalkenyl having at least one heteroatom in the ring. Heterocycloalkyls may be substituted or unsubstituted.

As used herein, a "lower" moiety (e.g., "lower" alkyl) is moiety having 1 to about 6, preferably 1 to about 4, carbon atoms.

As used herein, "pharmaceutically acceptable" means suitable for use in a human or other mammal.

As used herein, "safe and effective amount of a compound" (or composition, or the like) means an amount that is effective to exhibit biological activity, preferably wherein the biological activity is arresting and/or reversing hair loss or promoting hair growth, at the site(s) of activity in a mammalian subject, without undue adverse side effects (such as toxicity, irritation, or allergic response), commensurate with a reasonable benefit/risk ratio when used in the manner of this invention.

As used herein unless otherwise specified, the term "substituted" in reference to a group, moiety, or the like, means having one or more substituent groups each independently selected from hydrogen, alkyl, alkenyl, alkoxy, hydroxy, nitro, amino, alkylamino, cyano, halo, thiol, aryl, cycloalkyl, heteroaryl, heterocycloalkyl (e.g., piperidinyl, morpholinyl, pyrrolidinyl), imino, hydroxyalkyl, aryloxy, and arylalkyl, preferably hydrogen, alkyl, alkenyl, alkoxy, hydroxy, nitro, amino, alkylamino, halo, thiol, and aryloxy, more preferably hydrogen, alkyl, alkenyl, alkoxy, hydroxy, nitro, amino, alkylamino, and halo, even more preferably hydrogen, alkyl, and alkoxy, and most preferably alkoxy.

Compounds of the Present Invention

The compounds of the present invention have the structure:

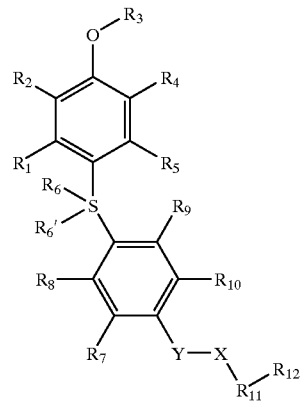

and pharmaceutically acceptable salts, hydrates, and biohydrolyzable amides, esters, and imides thereof, wherein:

(a) $R_1$, $R_2$, $R_5$, $R_7$, and $R_{10}$ are each, independently, selected from the group consisting of hydrogen, halogen, alkyl, alkenyl, alkynyl, heteroalkyl, heteroalkenyl, and heteroalkynyl;

(b) $R_4$ is selected from the group consisting of halogen, alkyl, alkenyl, alkynyl, cycloalkyl, cycloalkenyl, aryl, arylalkyl, heteroalkyl, heteroalkenyl, heteroalkynyl, heterocycloalkyl, heterocycloalkenyl, heteroaryl, heteroarylalkyl, and heteroarylalkenyl: wherein when $R_2$ is hydrogen. Y is —$CH_2CHK_1$, X is selected from the group consisting of —NZ— and —NH—, and $R_{12}$ is $C_1$–$C_4$ alkyl, wherein $K_1$ is selected from hydrogen and $C_1$–$C_4$ alkyl and Z is $C_1$–$C_4$ alkyl, then $R_4$ is not arylalkyl;

(c) $R_8$ and $R_9$ are each, independently, selected from the group consisting of hydrogen, halogen, alkyl, alkenyl, alkynyl, cycloalkyl, cycloalkenyl, aryl, arylalkyl, heteroalkyl, heteroalkenyl, heteroalkynyl, heterocycloalkyl, heterocycloalkenyl, heteroaryl, heteroarylalkyl, and heteroarylalkenyl, wherein at least one of $R_8$ and $R_9$ is not hydrogen;

(d) $R_3$ is selected from the group consisting of hydrogen, alkyl, alkenyl, alkynyl, cycloalkyl, cycloalkenyl, aryl, arylalkyl, heteroalkyl, heteroalkenyl, heteroalkynyl, heterocycloalkyl, heterocycloalkenyl, heteroaryl, heteroarylalkyl and heteroarylalkenyl;

(e) $R_6$ and $R_6'$ are each, independently, selected from the group consisting of nil and oxo;

(f) Y is selected from the group consisting of bond, alkyl, alkenyl, alkynyl, heteroalkyl, heteroalkenyl, and heteroalkynyl;

(g) X is selected from the group consisting of —NZ—, —NH— and —O—;

(h) $R_{11}$ is selected from the group consisting of bond and —C(O)—; wherein when Y is bond and X is —O—, then $R_{11}$ is —C(O)—;

(i) $R_{12}$ is selected from the group consisting of alkyl, alkenyl, alkynyl, heteroalkyl, heteroalkenyl, heteroalkynyl, cycloalkyl, cycloalkenyl, heterocycloalkyl, heterocycloalkenyl, aryl, arylalkyl, heteroaryl, heteroarylalkyl, and heteroarylalkenyl; or wherein when $R_{11}$ is bond, then $R_{12}$ and Z may be optionally bonded together to form a cycle selected from the group consisting of cycloalkyl, cycloalkenyl, heterocycloalkyl, heterocycloalkenyl, aryl, and heteroaryl: wherein when $R_{12}$ is heteroalkyl, heteroalkenyl, heteroalkynyl, heterocycloalkyl, heterocycloalkenyl, heteroaryl, heteroarylalkyl, or heteroarylalkenyl, then a heteroatom of $R_{12}$ is not directly covalently bonded to $R_{11}$; wherein when $R_{12}$ is heteroalkyl, heteroalkenyl, heteroalkynyl, heterocycloalkyl, heterocycloalkenyl, heteroaryl, heteroarylalkyl, or heteroarylalkenyl, then a heteroatom of $R_{12}$ is not directly coalently bonded to $R_{11}$; and wherein when $R_{11}$ is bond and X is —O—, then $R_{12}$ is not methyl; and (j) Z is selected from the group consisting of alkyl, alkenyl, alkynyl, heteroalkyl, heteroalkenyl, and heteroalkynyl; or wherein when $R_{11}$ is bond, then $R_{12}$ and Z may be optionally bonded together to form a cycle selected from the group consisting of cycloalkyl, cycloalkenyl, heterocycloalkyl, heterocycloalkenyl, aryl, and heteroaryl; wherein when $R_{12}$ is heteroalkyl, heteroalkenyl, heteroalkynyl, heterocycloalkyl, heterocycloalkenyl, heteroaryl, heteroarylalkyl or heteroarylalkenyl, then a heteroatom of $R_{12}$ is not directly covalently bonded to $R_{11}$.

The present compounds are sulfur-bridged compounds linked through a carbon atom which is substituted with substituents $R_6$ and/or $R_6'$. The remaining substituents, as well as $R_6$ and $R_6'$, are described in further detail below.

The Substituents $R_1$, $R_2$, $R_5$, $R_7$, and $R_{10}$

The substituents $R_1$, $R_2$, $R_5$, $R_7$, and $R_{10}$ each substitute on one of the phenyl rings of the structure shown herein. $R_1$, $R_2$, $R_5$, $R_7$, and $R_{10}$ are each, independently, selected from hydrogen, halogen, alkyl, alkenyl, alkynyl, heteroalkyl, heteroalkenyl, and heteroalkynyl.

$R_1$, $R_2$, $R_5$, $R_7$, and $R_{10}$ are preferably each, independently, selected from hydrogen, halogen, alkyl, alkenyl, heteroalkyl, and heteroalkenyl, $R_1$, $R_2$, $R_5$, $R_7$, and $R_{10}$ are more preferably each, independently, selected from hydrogen, halogen, and lower alkyl. Most preferably, $R_1$, $R_2$, $R_5$, $R_7$, and $R_{10}$ are each hydrogen.

The Substituent $R_4$

The substituent $R_4$ is selected from halogen, alkyl, alkenyl, alkynyl, cycloalkyl, cycloalkenyl, aryl, arylalkyl, heteroalkyl, heteroalkenyl, heteroalkynyl, heterocycloalkyl, heterocycloalkenyl, heteroaryl, heteroarylalkyl, and heteroarylalkenyl; wherein when $R_2$ is hydrogen. Y is —$CH_2CHK_1$, X is selected from the group consisting of —NZ— and —NH—, and $R_{12}$ is $C_1$–$C_4$ alkyl, wherein $K_1$ is selected from hydrogen and $C_1$–$C_4$ alkyl and Z is $C_1$–$C_4$ alkyl, then $R_4$ is not arylalkyl.

$R_4$ is preferably selected from halogen, alkyl, alkenyl, alkynyl, cycloalkyl, cycloalkenyl, aryl, heteroalkyl, heteroalkenyl, heteroalkynyl, heterocycloalkyl, heterocycloalkenyl, heteroaryl, heteroarylalkyl, and heteroarylalkenyl, $R_4$ is more preferably selected from halogen, alkyl, alkenyl, heteroalkyl, and heteroalkenyl, $R_4$ is even more preferably selected from halogen, alkyl, alkenyl, and heteroalkyl. $R_4$ is most preferably selected from halogen and lower alkyl. The most preferred halogens for $R_4$ are chlorine, bromine, and iodine, preferably chlorine and iodine, and most preferably iodine. The most preferred lower alkyls for $R_4$ are methyl, ethyl, iso-propyl, and tert-butyl, preferably methyl, iso-propyl, and tert-butyl, more preferably iso-propyl or tert-butyl. Most preferably, $R_4$ is lower alkyl, particularly iso-propyl or tert-butyl.

The Substituents $R_8$ and $R_9$ $R_8$ and $R_9$ are each, independently, selected from hydrogen, halogen, alkyl, alkenyl, alkynyl, cycloalkyl, cycloalkenyl, aryl, arylalkyl, heteroalkyl, heteroalkenyl, heteroalkynyl, heterocycloalkyl, heterocycloalkenyl, heteroaryl, heteroarylalkyl, and heteroarylalkenyl; wherein at least one of $R_8$ and $R_9$ is not hydrogen. Preferably, each of $R_8$ and $R_9$ are not hydrogen.

$R_8$ and $R_9$ are preferably each, independently, selected from halogen, alkyl, alkenyl, heteroalkyl, and heteroalkenyl. $R_8$ and $R_9$ are more preferably each, independently, selected from halogen, alkyl, alkenyl, and heteroalkyl. $R_8$ and $R_9$ are even more preferably each, independently, selected from halogen and lower alkyl. The most preferred halogens for $R_8$ and $R_9$ are chlorine and bromine, preferably chlorine. The most preferred lower alkyls for $R_8$ and $R_9$ are methyl, ethyl, iso-propyl, and tert-butyl, preferably methyl, iso-propyl, and tert-butyl, more preferably methyl and iso-propyl. Most preferably, $R_8$ and $R_9$ are each, independently, selected from lower alkyl and halogen, particularly methyl and chlorine, respectively.

The Substituent $R_3$ $R_3$ substitutes on the oxygen moiety of the biphenyl structure as shown above. $R_3$ is selected from hydrogen, alkyl, alkenyl, alkynyl, cycloalkyl, cycloalkenyl, aryl, arylalkyl, heteroalkyl, heteroalkenyl, heteroalkynyl, heterocycloalkyl, heterocycloalkenyl, heteroaryl, heteroarylalkyl and heteroarylalkenyl. Preferably, $R_3$ is selected from hydrogen, alkyl, alkenyl, cycloalkyl, aryl, arylalkyl, heteroalkyl, heteroalkenyl, heterocycloalkyl, heteroaryl, and heteroarylalkyl. More preferably, $R_3$ is selected from hydrogen, alkyl, alkenyl, aryl, arylalkyl, heteroalkyl, heteroaryl, and heteroarylalkyl. Still more preferably, $R_3$ is selected from hydrogen, alkyl, alkenyl, arylalkyl (preferably benzyl), heteroalkyl, and heteroarylalkyl. Even more preferably. $R_3$ is selected from hydrogen, lower alkyl, and lower alkenyl. Most preferably. $R_3$ is selected from hydrogen and lower alkyl. The most preferred lower alkyl for $R_3$ is methyl.

The Substituents $R_6$ and $R_6'$ $R_6$ and $R_6'$ are each, independently, selected from nil and oxo. Wherein both $R_6$ and $R_6'$ are nil, then the sulfur-bridge of the compound is —S—. Wherein $R_6$ is nil and $R_6'$ is oxo (or wherein $R_6$ is oxo and $R_6'$ is nil), then the sulfur-bridge of the compound is a sulfoxide (—S(O)—). Wherein $R_6$ and $R_6'$ are both oxo, then the sulfur-bridge of the compound is a sulfone (—S(O)(O)—).

The Substituent Y

Y is selected from bond, alkyl, alkenyl, alkynyl, heteroalkyl, heteroalkenyl, and heteroalkynyl. Wherein Y is bond, X is directly bonded to the phenyl ring bearing $R_7$, $R_8$, $R_9$, and $R_{10}$. Y is preferably selected from bond, alkyl, alkenyl, heteroalkyl, and heteroalkenyl. More preferably, Y is selected from bond and lower alkyl. Most preferably, Y is bond.

The Substituent X

X is selected from —NZ—, —NH—, and —O—. Z substitutes on the nitrogen of —NZ— and is selected from alkyl, alkenyl, alkynyl, heteroalkyl, heteroalkenyl, and heteroalkynyl; or wherein when $R_{11}$ is bond, then $R_{12}$ and Z may be optionally bonded together to form a cycle selected from cycloalkyl, cycloalkenyl, heterocycloalkyl, heterocycloalkenyl, aryl, and heteroaryl. Preferably, Z is selected from alkyl, alkenyl, heteroalkyl, and heteroalkenyl, or $R_{12}$ and Z are bonded together to form a cycle selected from cycloalkyl, cycloalkenyl, heterocycloalkyl, heterocycloalkenyl, aryl, and heteroaryl. More preferably, Z is lower alkyl, or $R_{12}$ and Z are bonded together to form a cycle selected from cycloalkyl, cycloalkenyl, heterocycloalkyl, heterocycloalkenyl, aryl, and heteroaryl. Most preferably, Z is $C_1$-$C_3$ alkyl, particularly methyl, or $R_{12}$ and Z are bonded together to form a cycle selected from cycloalkyl, cycloalkenyl, heterocycloalkyl, heterocycloalkenyl, aryl, and heteroaryl.

Preferably, X is selected from —NE— and —NZ—. Most preferably, X is —NH—, —N($CH_3$)—, or —NZ— wherein $R_{12}$ and Z are bonded together to form a cycle selected from the group consisting of cycloalkyl, cycloalkenyl, heterocycloalkyl, heterocycloalkenyl, aryl, and heteroaryl.

Wherein $R_{12}$ is bonded to Z to form a cycle, the cycle is preferably selected from cycloalkyl, heterocycloalkyl, aryl, and heteroaryl, more preferably from cycloalkyl, heterocycloalkyl, and aryl, even more preferably from cycloalkyl and heterocycloalkyl, and most preferably heterocycloalkyl. In addition to the optional substituents described herein above, the cycle may also optionally bear one or more oxo (i.e., doubly bonded oxygen) substituents. Non-limiting examples of these cycles include piperidinyl, morpholinyl, piperazinyl, pyrrolidinyl, indolinyl, succinimidyl, and hydantoinyl.

The Substituent $R_{11}$ $R_{11}$ is selected from bond and —C(O)—, wherein when Y is bond and X is —O—, then $R_{11}$ is —C(O)—. Wherein $R_{11}$ is bond, $R_{12}$ is directly bonded to X. While both bond and —C(O)— are both highly preferred for $R_{11}$, most preferably, $R_{11}$ is —C(O)—.

The Substituent $R_{12}$ $R_{12}$ is selected from alkyl, alkenyl, alkynyl, heteroalkyl, heteroalkenyl, heteroalkynyl, cycloalkyl, cycloalkenyl, heterocycloalkyl, heterocycloalkenyl, aryl, arylalkyl, heteroaryl, heteroarylalkyl, and heteroarylalkenyl; or wherein when $R_{11}$ is bond, then $R_{12}$ and Z may be optionally bonded together to form a cycle selected from the group consisting of cycloalkyl, cycloalkenyl, heterocycloalkyl, heterocycloalkenyl, aryl, and heteroaryl; wherein when $R_{12}$ is heteroalkyl, heteroalkenyl, heteroalkynyl, heterocycloalkyl, heterocycloalkenyl, heteroaryl, heteroarylalkyl, or heteroarylalkenyl, then a heteroatom of $R_{12}$ is not directly covalently bonded to $R_{11}$. Accordingly, carbamates and ureas at the —Y—X—$R_{11}$-$R_{12}$ linkage are not contemplated within the present invention. For example, wherein $R_{12}$ is heteroalkyl, it is not, e.g., —O—$CH_2$—$CH_3$, but could be, e.g., —$CH_2$—O—$CH_3$.

Preferably, $R_{12}$ is selected from alkyl, alkenyl, heteroalkyl, heteroalkenyl, cycloalkyl, cycloalkenyl, heterocycloalkyl, heterocycloalkenyl, aryl, arylalkyl, heteroaryl, heteroarylalkyl, and heteroarylalkenyl, or is bonded to Z to form a cycle selected from cycloalkyl, cycloalkenyl, heterocycloalkyl, heterocycloalkenyl, aryl, and heteroaryl. More preferably, $R_{12}$ is selected from alkyl, alkenyl, heteroalkyl, heteroalkenyl, aryl, arylalkyl, heteroaryl, heteroarylalkyl, and heteroarylalkenyl, or is bonded to Z to form a cycle selected from cycloalkyl, cycloalkenyl, heterocycloalkyl, heterocycloalkenyl, aryl, and heteroaryl. Even more preferably, $R_{12}$ is selected from alkyl, heteroalkyl, arylalkyl, and heteroarylalkyl, or is bonded to Z to form a cycle selected from cycloalkyl, cycloalkenyl, heterocycloalkyl, heterocycloalkenyl, aryl, and heteroaryl. Most preferably, $R_{12}$ is lower alkyl, or is bonded to Z to form a cycle selected from cycloalkyl, cycloalkenyl, heterocycloalkyl, heterocycloalkenyl, aryl, and heteroaryl. The most preferred lower alkyls for $R_{12}$ are methyl, ethyl, n-propyl, iso-propyl, n-butyl, tert-butyl, and n-pentyl, particularly methyl, n-propyl, iso-propyl, n-butyl, and tert-butyl.

Wherein $R_{12}$ is bonded to Z to form a cycle, the cycle is preferably selected from cycloalkyl, heterocycloalkyl, aryl, and heteroaryl, more preferably from cycloalkyl, heterocycloalkyl, and aryl, even more preferably from cycloalkyl and heterocycloalkyl, and most preferably heterocycloalkyl. In addition to the optional substituents described herein above, the cycle may also optionally bear one or more oxo (i.e., doubly bonded oxygen) substituents. Non-limiting examples of these cycles include piperidinyl, morpholinyl, piperazinyl, pyrrolidinyl, indolinyl, succinimidyl, and hydantoinyl.

Preferred compounds of the present invention are set forth in the following tables:

TABLE 1

Preferred Compounds of the Present Invention
In the following preferred compounds, $R_6$ and $R_6'$ are each nil:

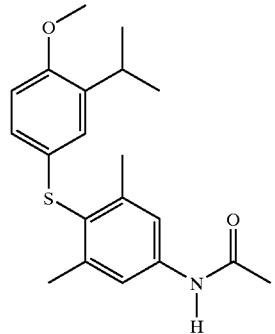

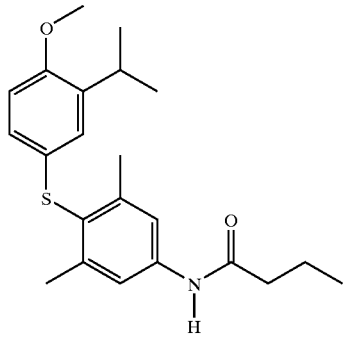

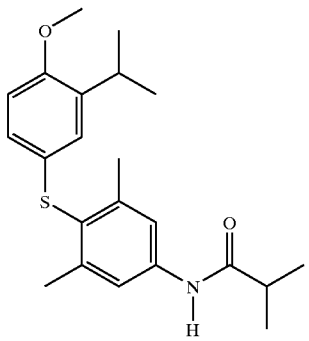

TABLE 1-continued
Preferred Compounds of the Present Invention
In the following preferred compounds, $R_6$ and $R_6'$ are each nil:
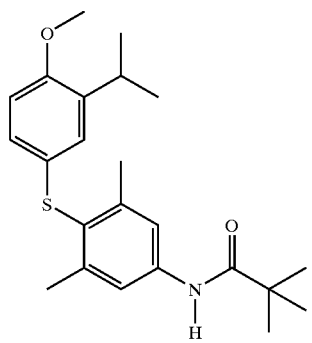
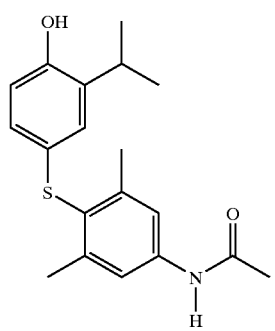
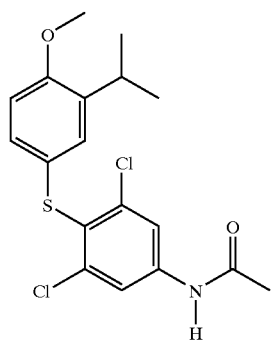
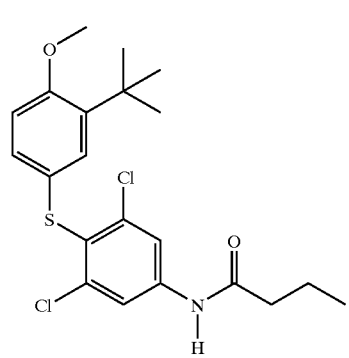
TABLE 1-continued
Preferred Compounds of the Present Invention
In the following preferred compounds, $R_6$ and $R_6'$ are each nil:
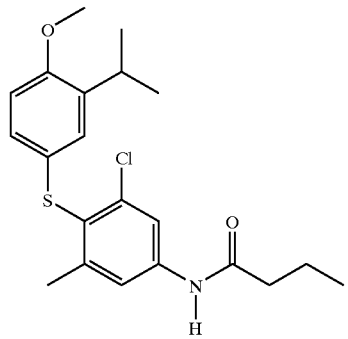
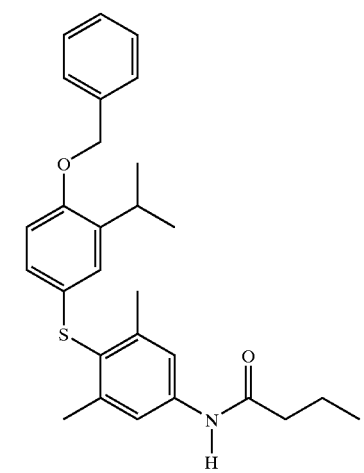
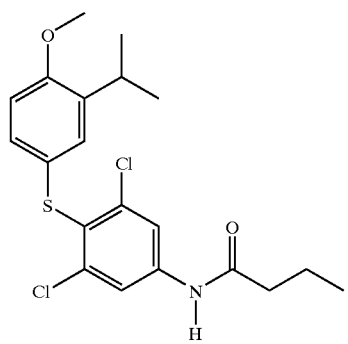
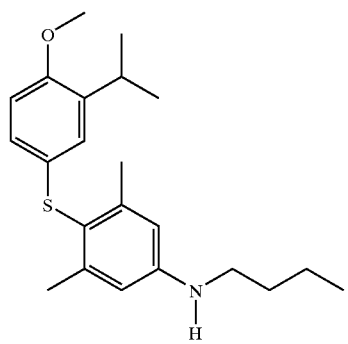

TABLE 1-continued
Preferred Compounds of the Present Invention
In the following preferred compounds, $R_6$ and $R_6'$ are each nil:
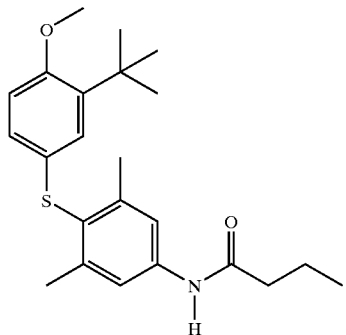
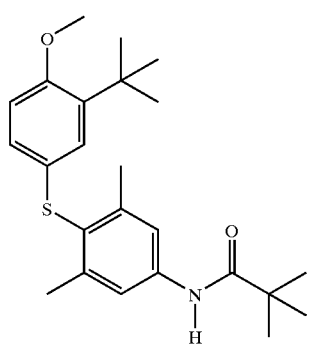
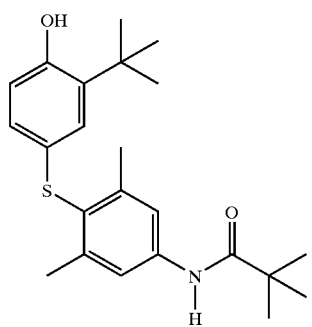
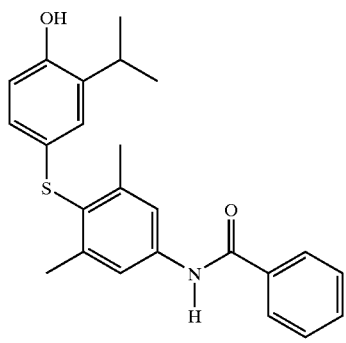
TABLE 1-continued
Preferred Compounds of the Present Invention
In the following preferred compounds, $R_6$ and $R_6'$ are each nil:
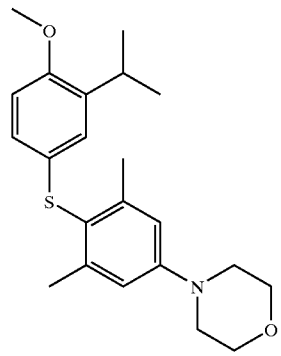
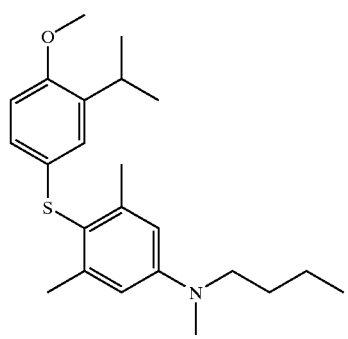
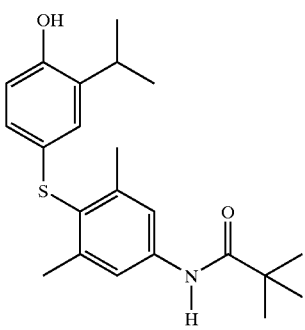
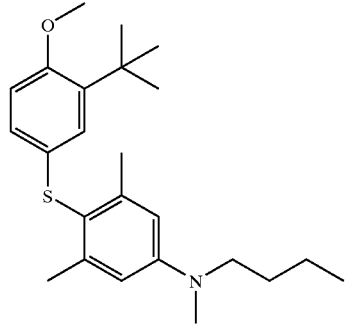

TABLE 1-continued

Preferred Compounds of the Present Invention
In the following preferred compounds, $R_6$ and $R_6'$ are each nil:

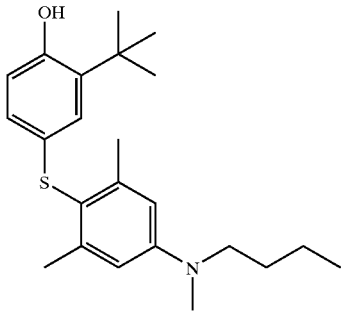

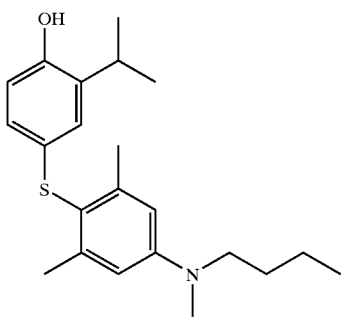

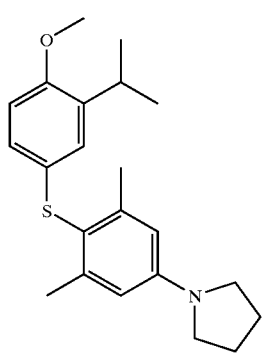

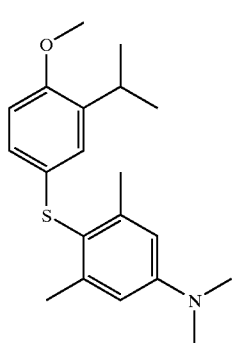

TABLE 1-continued

Preferred Compounds of the Present Invention
In the following preferred compounds, $R_6$ and $R_6'$ are each nil:

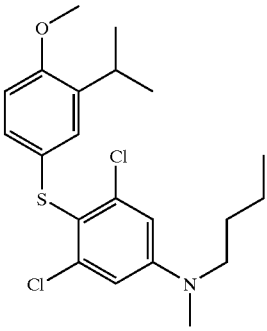

TABLE 2

Preferred Compounds of the Present Invention
In the following preferred compounds, $R_6$ is nil and $R_6'$ is oxo
(or $R_6$ is oxo and $R_6'$ is nil):

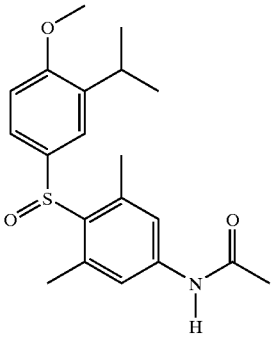

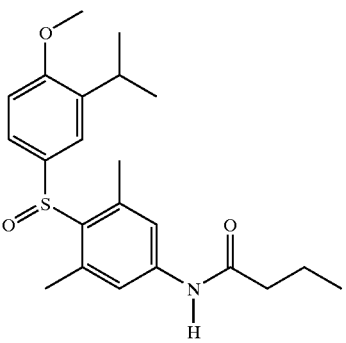

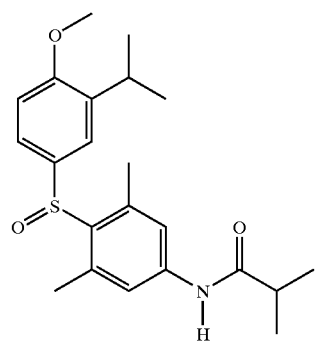

TABLE 2-continued
Preferred Compounds of the Present Invention
In the following preferred compounds, $R_6$ is nil and $R_6'$ is oxo
(or $R_6$ is oxo and $R_6'$ is nil):
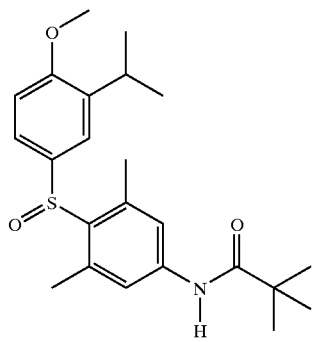
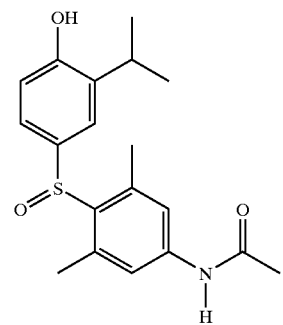
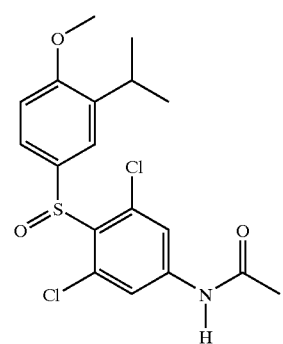
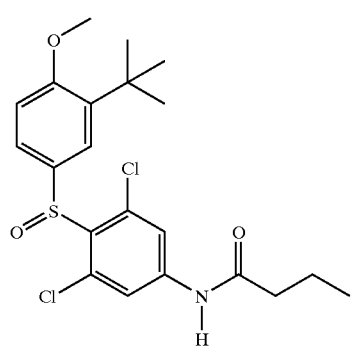
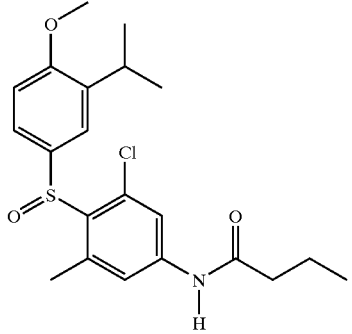
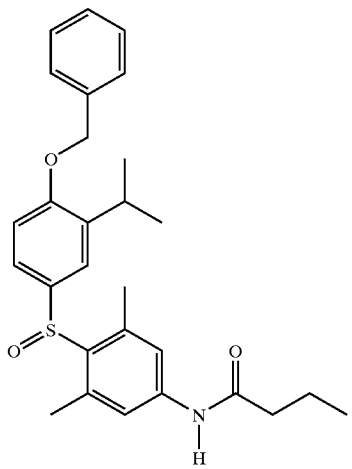
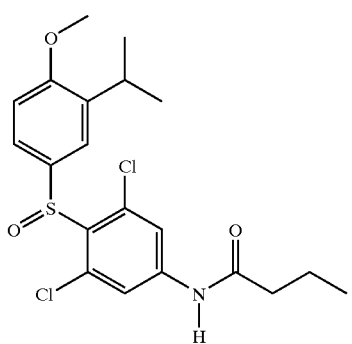
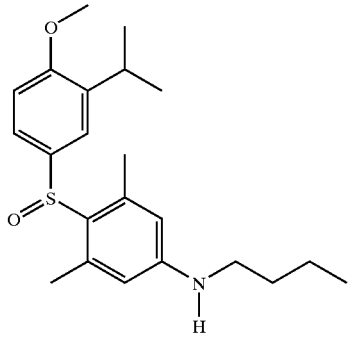

TABLE 2-continued
Preferred Compounds of the Present Invention
In the following preferred compounds, $R_6$ is nil and $R_6'$ is oxo
(or $R_6$ is oxo and $R_6'$ is nil):
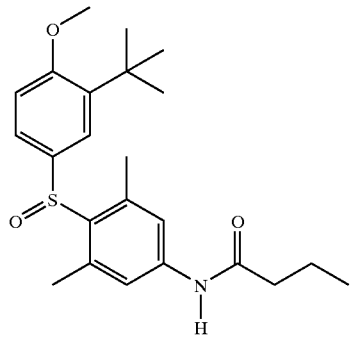
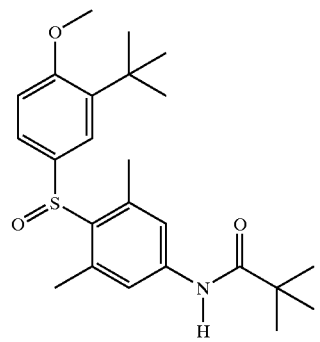
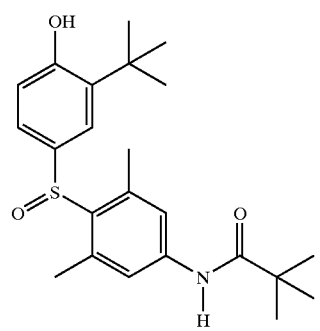
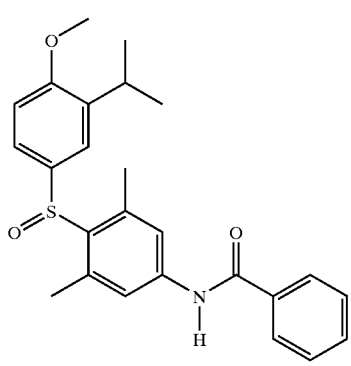
TABLE 2-continued
Preferred Compounds of the Present Invention
In the following preferred compounds, $R_6$ is nil and $R_6'$ is oxo
(or $R_6$ is oxo and $R_6'$ is nil):
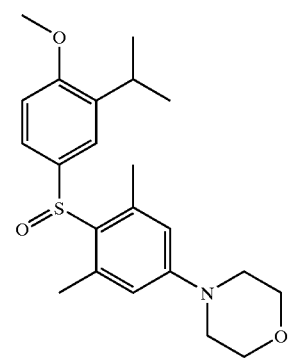
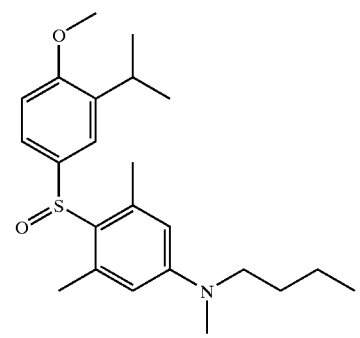
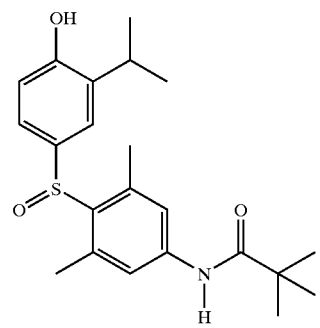
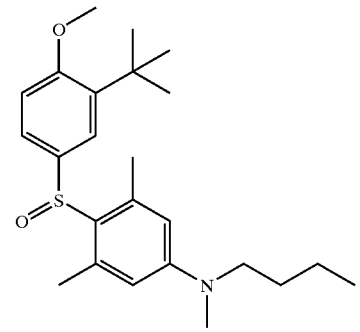

TABLE 2-continued

Preferred Compounds of the Present Invention
In the following preferred compounds, $R_6$ is nil and $R_6'$ is oxo
(or $R_6$ is oxo and $R_6'$ is nil):

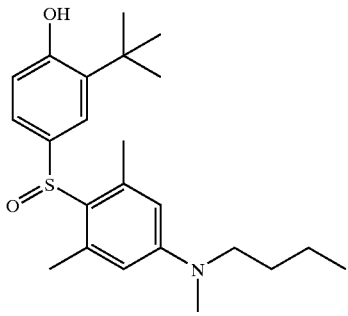

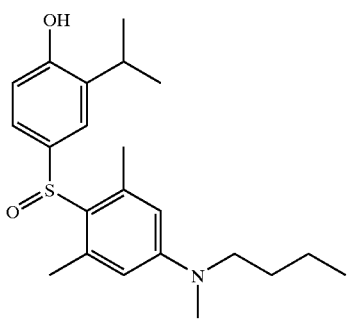

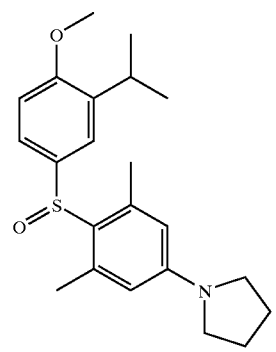

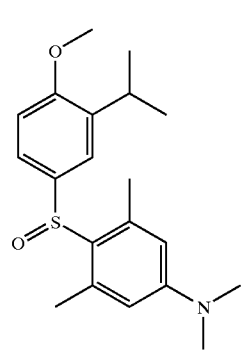

TABLE 2-continued

Preferred Compounds of the Present Invention
In the following preferred compounds, $R_6$ is nil and $R_6'$ is oxo
(or $R_6$ is oxo and $R_6'$ is nil):

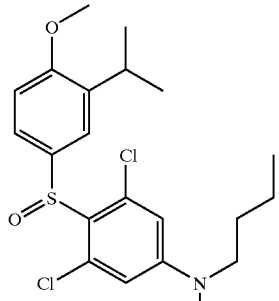

TABLE 3

Preferred Compounds of the Present Invention
In the following preferred compounds, $R_6$ and $R_6'$ are each oxo:

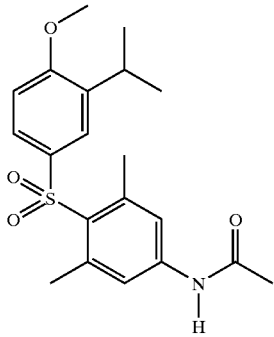

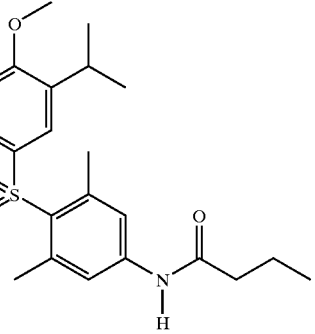

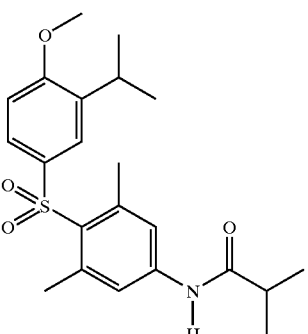

TABLE 3-continued
Preferred Compounds of the Present Invention
In the following preferred compounds, $R_6$ and $R_6'$ are each oxo:
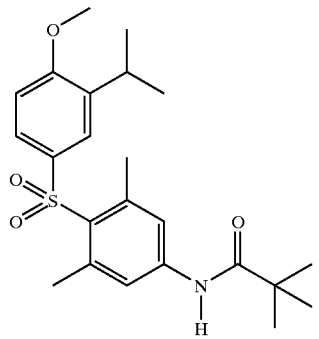
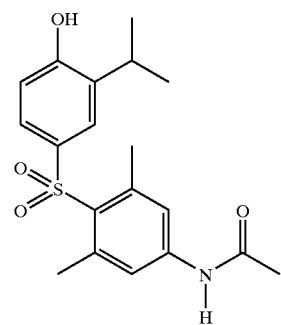
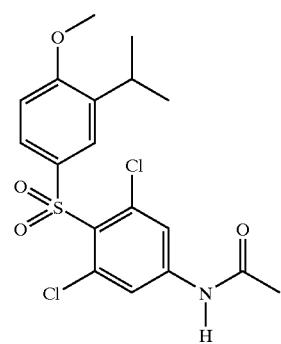
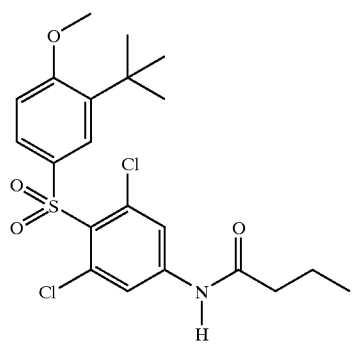
TABLE 3-continued
Preferred Compounds of the Present Invention
In the following preferred compounds, $R_6$ and $R_6'$ are each oxo:
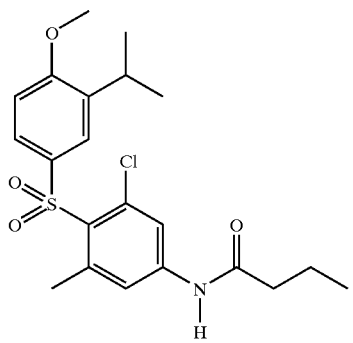
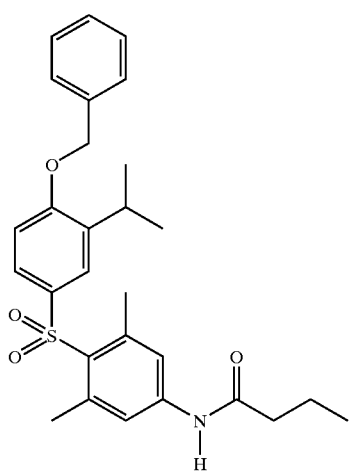
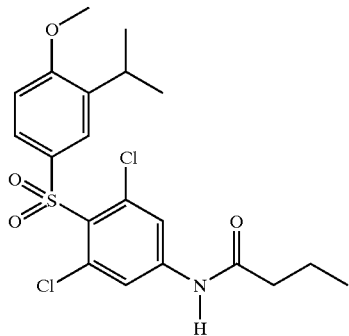
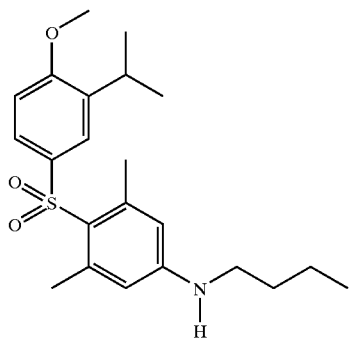

TABLE 3-continued
Preferred Compounds of the Present Invention
In the following preferred compounds, $R_6$ and $R_6'$ are each oxo:
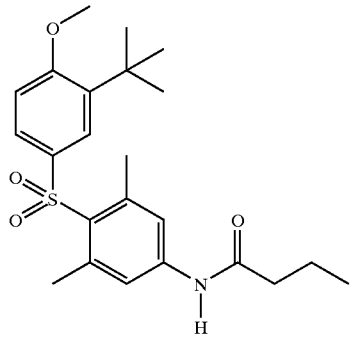
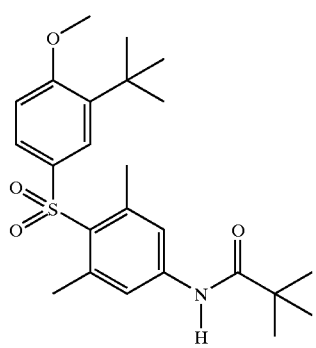
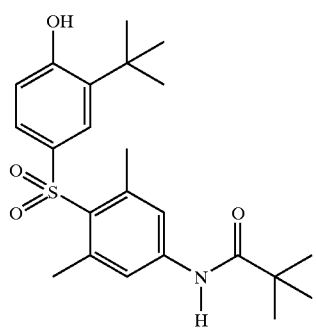
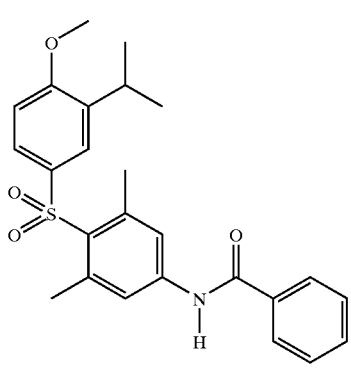
TABLE 3-continued
Preferred Compounds of the Present Invention
In the following preferred compounds, $R_6$ and $R_6'$ are each oxo:
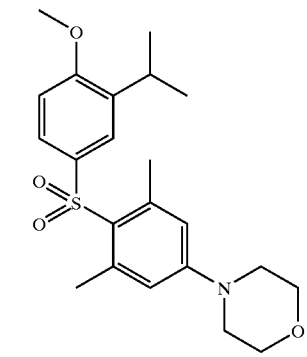
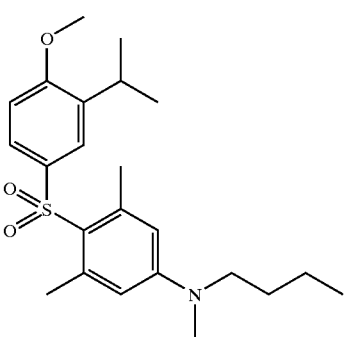
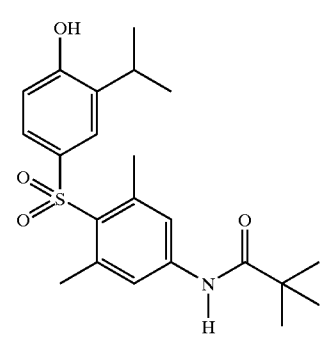
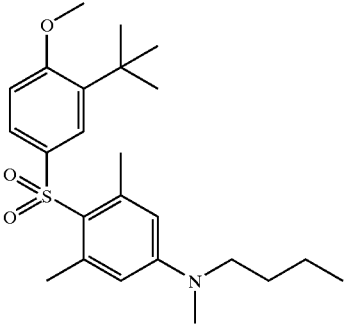

TABLE 3-continued

Preferred Compounds of the Present Invention
In the following preferred compounds, $R_6$ and $R_6'$ are each oxo:

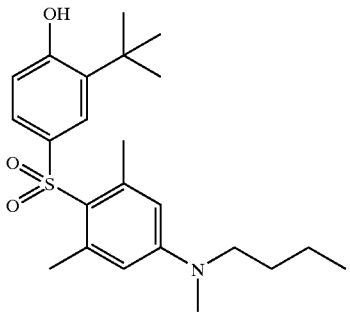

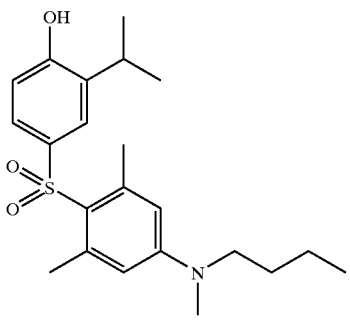

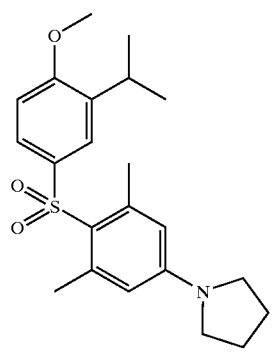

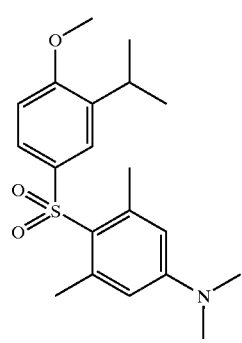

TABLE 3-continued

Preferred Compounds of the Present Invention
In the following preferred compounds, $R_6$ and $R_6'$ are each oxo:

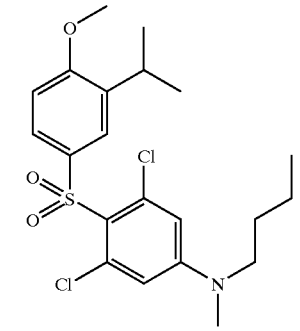

Analytical Methods

The present invention relates to compounds and methods for treating hair loss. Preferably, the compound utilized in the present invention will be cardiac-sparing. Compounds (test compounds) may be tested for their ability to induce anagen and their lack of cardiotoxicity (cardiac-sparing) using the following methods. Alternatively, other methods well-known in the art may be used (but with the term "cardiac-sparing" being defined according to the method disclosed herein below).

Cardiotoxicity Assay:

The cardiotoxicity assay measures the potential of a test compound to adversely affect the cardiovascular system. As thyroid hormone (T3) damages the cardiovascular system, the heart enlarges. See, e.g., Gomberg-Maitland et al., "Thyroid hormone and Cardiovascular Disease", *American Heart Journal*, Vol. 135(2), pp. 187–196 (1998); Klein and Ojamaa, "Thyroid Hormone and the Cardiovascular System", *Current Opinion in Endocrinology and Diabetes*, Vol. 4, pp.341–346 (1997); and Klemperer et al., "Thyroid Hormone Therapy and Cardiovascular Disease", *Progress in Cardiovascular Diseases*, Vol. 37 (4), pp. 329–336 (1996). This increases the weight of the heart relative to whole body weight. The cardiotoxicity assay herein below is used to test compounds for potentially adverse cardiac effects by measuring their effect on the heart-to-body weight ratio.

Two groups each of six male Sprague Dawley rats (Harlan Sprague Dawley, Inc., Indianapolis, Ind.) (each weighing from approximately 220 grams to 235 grams) are utilized. The first group is a vehicle control group and the second group is a test compound group. The length of the assay is 30 days, with treatment of vehicle or test compound in vehicle daily for 28 of those days as described below.

Prior to initiation of the assay, each rat is allowed to acclimate to standard environmental conditions for 5 days. Each rat receives food (standard rat chow diet) and water ad libitum 5 days prior to initiation of the assay as well as to termination of the study.

The vehicle is 91:9 (v:v) propylene glycol:ethanol. The test compound is prepared at a concentration of 500 µg/mL in the vehicle.

Each rat is weighed on day 1 of the assay. Dosage calculations are then performed: each rat will be administered daily a dosing solution of vehicle or test compound in vehicle (depending on whether the rat is in the vehicle control group or the test compound group, respectively) at 500 µL of dosing solution per kg of rat. For rats in the test compound group, this corresponds to a dose of 250 µg of test compound per kg of rat.

Day 2 is the first day of treatment with dosing solution for both groups. Body weights are taken for each rat on days 3, 5, 8, 10, 12, 15, 17, 19, 22, 24, 26, and 29 prior to dosing for that day; for each rat, the dosing solutions are recalculated and administered accordingly upon change in body weight.

Treatment occurs once daily in the morning on days 2 through 29, inclusive, for each rat in each group. For each treatment, the dosing solution is administered subcutaneously between the shoulders of the rat such that the injection sites are rotated in this area.

On day 30 in the morning, the rats of each group are euthanized with $CO_2$ from dry ice. Each rat is immediately weighed for total body weight.

The hearts of each rat are then excised as follows. An incision is made to expose the abdominal cavity. The rib cage is carefully cut at the sternum with small scissors, such that the heart and lungs are exposed. With small scissors and forceps, the vessels connected to the heart are cut away from the heart. These vessels include the caudal vena cava, left cranial vena cava (pulmonary trunk), right cranial vena cava, thoracic aorta, right subclavian artery, internal thoracic artery and vein, and any other small attachments. The heart is then immediately taken out intact, including the left and right auricles and left and right ventricles. Immediately thereafter, any excess tissue is trimmed away, the heart is lightly blotted on a paper towel until no more blood is visibly left behind on the paper towel, and the heart is weighed.

The heart weight is divided by the body weight after euthanization for each rat to give the heart/body ratio. The heart/body ratios for each rat in the vehicle control group are added together and divided by 6 (i.e., the total number of rats in the group) to give RV (ratio for vehicle control group). Similarly, the heart/body ratios for each rat in the test compound group are added together and divided by 6 to give RT (ratio for test compound group).

The index C is then calculated by dividing RT by RV. As defined herein, where C is less than 1.3, the test compound is cardiac-sparing. Preferably. C is less than 1.2, more preferably less than 1.15, and most preferably less than 1.1. In accordance with this method, T3 and T4 are not cardiac-sparine.

Telogen Conversion Assay:

The Telogen Conversion Assay measures the potential of a test compound to convert mice in the resting stage of the hair growth cycle ("telogen"), to the growth stage of the hair growth cycle ("anagen").

Without intending to be limited by theory, there are three principal phases of the hair growth cycle: anagen, catagen, and telogen. It is believed that there is a longer telogen period in C3H mice (Harlan Sprague Dawley, Inc., Indianapolis. Ind.) from approximately 40 days of age until about 75 days of age, when hair growth is synchronized. It is believed that after 75 days of age, hair growth is no longer synchronized. Wherein about 40 day-old mice with dark fur (brown or black) are used in hair growth experiments, melanogenesis occurs along with hair (fur) growth wherein the topical application of hair growth inducers are evaluated. The Telogen Conversion Assay herein below is used to screen compounds for potential hair growth by measuring melanogenesis.

Three groups of 44 day-old C3H mice are utilized: a vehicle control group and a test compound group, wherein the test compound group is administered a compound according to the present invention. The length of the assay is at least 19 days with 15 treatment days (wherein the treatment days occur Mondays through Fridays). Day 1 is the first day of treatment. Most studies will end on Day 19, but a few may be carried out to Day 24 if the melanogenesis response looks positive, but occurs slowly. A typical study design is shown in Table 4 below. Typical dosage concentrations are set forth in Table 4, however the ordinarily skilled artisan will readily understand that such concentrations may be modified.

TABLE 4

| Group # | Animal # | Compound | Concentration | Application volume | Length of Study |
|---|---|---|---|---|---|
| 1 | 1–10 | Test Compound | 0.1% in vehicle** | 400 µL topical | 19 or 24 days |
| 2 | 11–20 | Positive Control (T3) | 0.01% in vehicle** | 400 µL topical | 19 or 24 days |
| 3 | 21–30 | Vehicle** | N/A | 400 µL topical | 19 or 24 days |

**The vehicle is 60% ethanol, 20% propylene glycol, and 20% dimethyl isosorbide (commercially available from Sigma Chemical Co., St. Louis, MO).

The mice are treated topically Monday through Friday on their lower back (base of tail to the lower rib). A pipettor and tip are used to deliver 400 µL to each mouse's back. The 400 µL application is applied slowly while moving hair on the mouse to allow the application to reach the skin.

While each treatment is being applied to the mouse topically, a visual grade of from 0 to 4 will be given to the skin color in the application area of each animal. As a mouse converts from telogen to anagen, its skin color will become more bluish-black. As indicated in Table 5, the grades 0 to 4 represent the following visual observations as the skin progresses from white to bluish-black.

TABLE 5

| Visual Observation | Grade |
|---|---|
| Whitish Skin Color | 0 |
| Skin is light gray (indication of initiation of anagen) | 1 |
| Appearance of Blue Spots | 2 |
| Blue Spots are aggregating to form one large blue area | 3 |
| Skin is dark blue (almost black) with color covering majority of treatment area (indication of mouse in full anagen) | 4 |

Methods of Making

The compounds of the present invention are prepared according to, methods which are well-known to those ordinarily skilled in the art. The starting materials used in preparing the compounds of the invention are known, made by known methods, or are commercially available as a starting material.

It is recognized that the ordinarily skilled artisan in the art of organic chemistry can readily carry out standard manipulations of organic compounds without further direction. Examples of such manipulations are discussed in standard texts such as J. March, *Advanced Organic Chemistry*, John Wiley & Sons, 1992.

The ordinarily skilled artisan will readily appreciate that certain reactions are best carried out when other functionalities are masked or protected in the compound, thus increasing the yield of the reaction and/or avoiding any undesirable side reactions. Often, the ordinarily skilled artisan utilizes protecting groups to accomplish such increased yields or to avoid the undesired reactions. These reactions are found in the literature and are also well within the scope of the ordinarily skilled artisan. Examples of many such manipulations can be found in, for example, T. Greene, *Protecting Groups in Organic Synthesis*, John Wiley & Sons, 1981.

The compounds of the present invention may have one or more chiral center. As a result, one may selectively prepare one optical isomer, including diastereomers and enantiomers, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastercomers and enantiomers, or stereoisomers may be separated using known methods, such as through the use of, for example, chiral salts and chiral chromatography.

In addition, it is recognized that one optical isomer, including a diastereomer and enantiomer, or a stereoisomer, may have favorable properties over the other. Thus, when disclosing and claiming the invention, when one racemic mixture is disclosed, it is clearly contemplated that both optical isomers, including diastercomers and enantiomers, or stereoisomers substantially free of the other are disclosed and claimed as well.

The compounds of the present invention may be prepared using a variety of procedures known to those ordinarily skilled in the art. Non-limiting general preparations include the following.

The compounds of the invention can be prepared, after removal of temporary protection groups (see, e.g., T. Greene, *Protecting Groups in Organic Synthesis*, John Wiley & Sons, 1981) by condensing (e.g., acylating or alkylating) a compound of the structure:

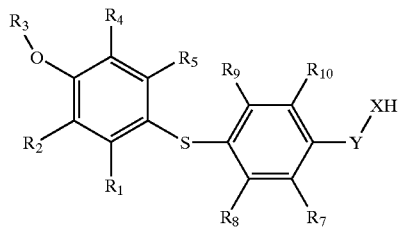
(I)

wherein $R_1$, $R_2$, $R_3$, $R_4$, $R_5$, $R_7$, $R_8$, $R_9$, $R_{10}$, Y, and X are defined herein above and are in an appropriately protected form if necessary, with a reactive derivative of the structure:

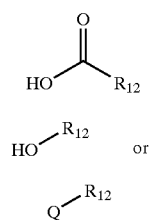

(II)
(III)
or
(IV)

wherein $R_{12}$ is defined herein above and is in an appropriately protected form if necessary and Q is halogen, preferably bromine or iodine, and most preferably iodine. Reactive derivatives of structure II include, for example, activated esters such as 1-hydroxybenzotriazole esters, mixed anhydrides of organic or inorganic acids such as hydrochloric acid and sulfonic acids, and symmetrical anhydrides of the acids of structure II. Activated derivatives of structure III include trifluoromethane sulfonyl esters and other activated derivatives known to those ordinarily skilled in the art.

Compounds of structure Iv are generally appropriately reactive without further modification; however, it may be necessary to convert a less reactive halogen to a more reactive halogen such as bromine or iodine as is known by those ordinarily skilled in the art. Many appropriately activated derivatives of structure II, III, or IV are commercially available and others can be prepared by methods known to those ordinarily skilled in the art. Non-limiting examples of condensations of this type are provided in Examples 2, 3, 4, 5, 7, 9, and 10.

Additionally, appropriately protected compounds resulting from the condensation of a compound of structure I with a compound of structure II, III or IV may be further modified to afford additional compounds of the invention after removal of temporary protection groups. These modifications include, but are not limited to, reduction of an amide to an amine as described in Example 6 to afford a secondary or tertiary amine, and alkylation of an amide as described in Example 6.

Furthermore, compounds of the invention, in an appropriately protected form if necessary and having the thioether linkage, may be oxidized using conditions known to those ordinarily skilled in the art to afford sulfones of the structure V and sulfoxides of the structure VI (see structures below), also compounds of the invention after removal of temporary protection groups. A specific example of the oxidation of a thioether to the sulfone using tert-butylhydroperoxide is described in Example 13 and specific examples of the oxidation of a thioether to the sulfoxide using 3-chloroperoxybenzoic acid are described in Examples 11 and 12.

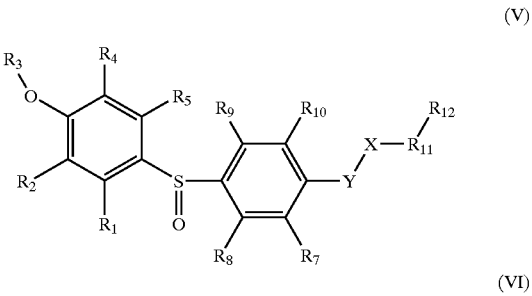
(V)

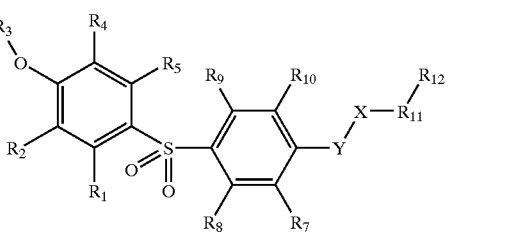
(VI)

Additionally, compounds of the structure I may be prepared from a biaryl thioether intermediate of structure VII wherein P is, for example, a nitro, cyano, or acyl group.

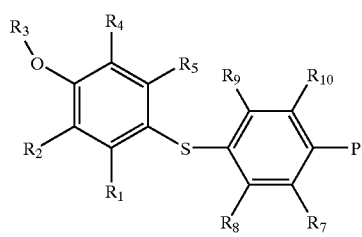

Compounds of the structure VII may be prepared by condensing a 4-halonitrobenzene of structure VIII with an appropriately substituted phenol of structure IX in a base catalyzed reaction as described in Examples 1, 7 and 8 below wherein Q is preferably chlorine or bromine.

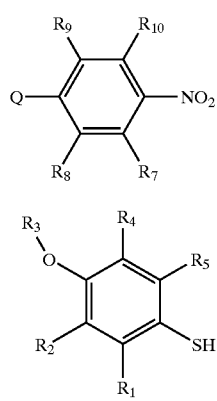

Compounds of the structure VII can be converted to compounds of the structure I by further transformation. For example, wherein P is nitro, the resulting compound of structure VII may be converted into a compound of structure I by reduction to the amine using standard chemical reactions. Wherein P is an acyl group, the compounds may be converted to compounds of structure I having secondary or tertiary amines by reductive alkylation of the ketone with a primary or secondary amine and a borohydride reducing reagent in a solvent such as trimethylorthoformate using conditions known to those ordinarily skilled in the art.

For even further guidance, the following non-limiting examples illustrate more specifically the methods of making various compounds of the present invention.

As used herein, the following abbreviations are used:

| | |
|---|---|
| Tetrahydrofuran | THF |
| N,N-Dimethylformamide | DMF |
| N-tert-butoxycarbonyl | BOC |
| N,N-diisopropylethylamine | i-Pr$_2$NEt or i-Pr$_2$EtN |
| Trifluoroacetic acid | TFA |
| 18-Crown-6 | 1, 4, 7, 10, 13, 16-hexaoxacyclooctadecane |

Example 1

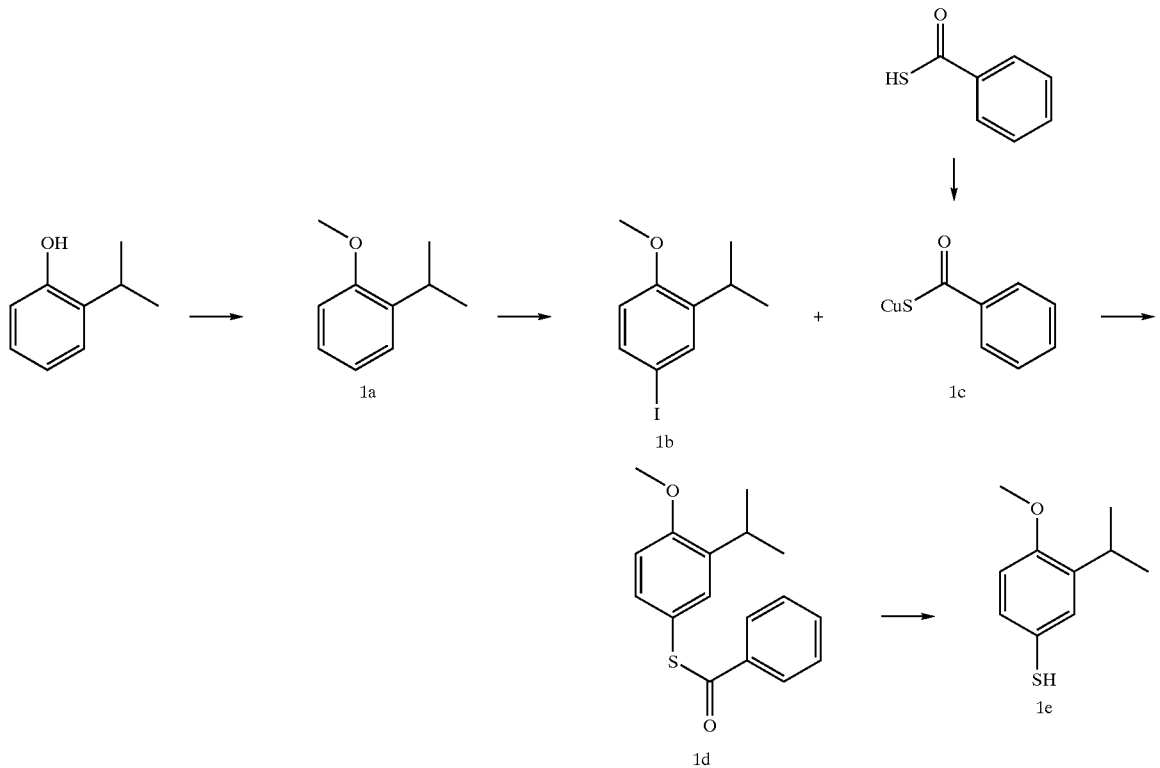

-continued

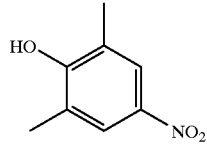 → 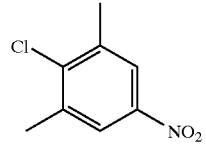 + 1e → 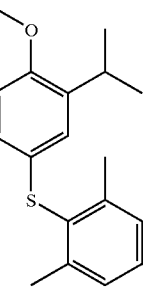

1g

→ 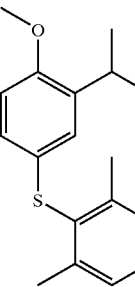

1h 1a. 2-iso-propyl anisole: Potassium hydroxide (5.6 g) is added to 13.4 mL acetone followed by 2-iso-propylphenol (13.6 g). After the potassium hydroxide is dissolved, methyl iodide (14.2 g) is added. The reaction is refluxed overnight, 150 mL of water is added. This reaction is extracted 3 times with 100 mL diethyl ether. The organic layer is extracted twice with 100 mL 10% sodium hydroxide in water, once with 100 mL water, and once with 100 mL saturated ammonium chloride. After drying over magnesium sulfate, the organic solution is dried over MgSO$_4$, filtered, and concentrated under reduced pressure. The material is fractionally distilled under reduced pressure to afford 1a.

1b. 3-iso-propyl-4-methoxyiodobenzene: Potassium iodide (8.85 g) is suspended in 80 mL of dichloromethane. The mixture is cooled to 0° C. and then 18-crown-6 (0.7 g) in 20 mL dichloromethane is added. In 100 mL dichloromethane, 3-chloroperbenzoic acid is added. To this mixture is added 2-iso-propyl anisole (1a; 4 g) dropwise. The reaction is stirred for 3 hours in a 0° C. bath and then is poured into 300 mL of ice water and stirred for an additional 30 minutes. At this time, the organic layer is isolated and washed with 200 mL saturated sodium hydrogen carbonate solution, followed by 200 mL water, and is dried over magnesium sulfate, filtered, and concentrated under reduced pressure. The compound is purified by chromatography on silica gel (hexane:ethyl acetate) to afford 1b.

1c. Copper (I) thiobenzoate: Copper (II) acetate (3 g) is dissolved in 100 mL glacial acetic acid. Thiobenzoic acid (1.25 g) is dissolved in 25 mL glacial acetic acid and this is poured into the copper (II) acetate solution. Precipitate is formed and is isolated by filtration. The solid is washed with acetic acid, water, and ethanol, and then dried under reduced pressure to afford 1c.

1d. S-benzoyl-3-iso-propyl-4-methoxythiophenol: Copper (I) thiobenzoate (1c; 0.141 g) and 3-iso-propyl-4-methoxyiodobenzene (0.6 g) are dissolved in 9 mL hexamethylphosphoramide. The reaction is heated at about 100° C. for 2 hours and then poured into 500 mL water. The mixture is stirred until precipitation is complete and the precipitate is isolated and washed with water and air dried. This material is extracted in a Soxhlet extractor using benzene and concentrated under reduced pressure. The residue is triturated with hexane to afford 1d. The material can be further purified by crystallization from ethyl acetate:hexane.

1e. 3-iso-propyl-4-methoxythiophenol: S-benzoyl-3-iso-propyl-4-methoxythiophenol (0.5 g) in 25 mL 10% aqueous sodium hydroxide and 2.5 mL ethanol is heated to reflux under nitrogen for about 16 hours. The mixture is cooled and extracted once with ethyl acetate. The aqueous phase is acidified with 6 N HCl and then extracted twice with ethyl acetate. The organic layers are combined and washed with water and brine then dried over sodium sulfate and filtered. The filtrate is concentrated under reduced pressure and purified by chromatography on silica gel (hexane:ethyl acetate) to afford 1e.

1f. 4-chloro-3,5-dimethyl-nitrobenzene: 2',6'-dimethyl-4-nitrophenol (3 g) is added to 50 mL dichloromethane followed by addition of 3.6 mL pyridine. The solution is cooled to 0° C. and 3.6 mL trifluoromethanesulfonic anhydride is added dropwise over 20 minutes. The reaction is mixed for about 3 hours at 0° C. 25 mL water is added to quench the reaction. The organic layer is extracted twice with 25 mL 1N hydrochloric acid, twice with 25 mL water, twice with 25 mL 1N sodium hydroxide, twice with 25 mL water, dried with magnesium sulfate, and concentrated under reduced pressure. The remaining residue is dissolved in 40 mL of DMF followed by addition of lithium chloride (2.4 g). The mixture is refluxed for 17 hours at 150° C. The mixture is concentrated under high vacuum. To this residue, 60 mL water and 60 mL ethyl acetate is added and stirred. This mixture is filtered, the organic layer separated, and dried with magnesium sulfate. The organic layer is concentrated under high vacuum and the remaining residue presorbed to silica gel using dichloromethane. The presorbed residue is then purified by chromatography on silica gel (hexane:ethyl acetate) and subsequently crystallized from hexanes to afford 1f.

1g. 3,5-dimethyl-4-(4'-methoxythiophenoxy)-nitrobenzene: 4-chloro-3,5-dimethyl-nitrobenzene (1f; 175 mg) and 3-iso-propyl-4-methoxythiophenol (1e; 139 mg) are dissolved into 7.5 mL methylsulfoxide. To this solution, anhydrous potassium carbonate (153 mg) is added and the reaction is mixed under nitrogen for 23 hours at 128° C. The reaction is precipitated by the addition of 50 mL ice water. The mixture is then extracted with 75 mL ethyl acetate. The organic layer is extracted once with 50 mL brine solution, dried with magnesium sulfate, and concentrated under high vacuum to afford 1g.

1h. 2',6'-dimethyl-3-iso-propyl-4-methoxy-4'-aminodiphenylthioether: 3.5-dimethyl-4-(4'-methoxythiophenoxy)-nitrobenzene (1g, 200 mg) is dissolved in 15 mL ethanol and 10% palladium on carbon is added. The reaction is hydrogenated, then filtered through Celite and concentrated under reduced pressure to afford 1h. Alternatively, 3.5-dimethyl-4-(4'-methoxythiophenoxy)-nitrobenzene (1g; 0.33 g) is dissolved in 5 mL of 49:1 ethanol:ethyl acetate by heating on a water bath (40° C.) and to this solution, tin chloride dihydrate (1 g) is added. The reaction is heated to 70° C. and stirred for about 2 hours. The reaction is allowed to cool to room temperature, then poured onto ice. The pH is made slightly basic (pH 7–8) by addition of 5% aqueous sodium bicarbonate (50 mL) and then extracted with ethyl acetate (50 mL). The organic phase is washed with brine (50 mL), treated with charcoal, dried over MgSO$_4$, and filtered. The filtrate is evaporated to provide 1h.

Alternative preparation of 1e

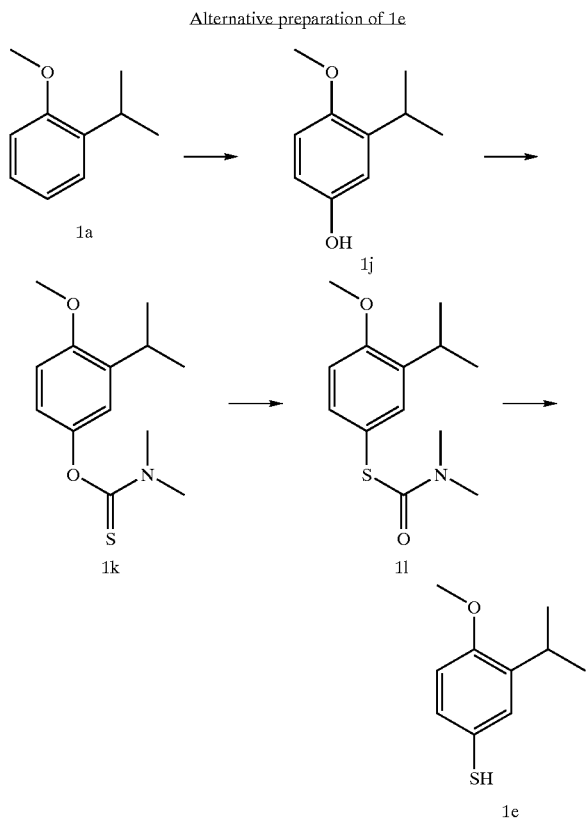

1j. 3-iso-propyl-4-methoxyphenol: Acetyl chloride (5.9 mL) is added to 200 mL dichloromethane. To this solution is added trifluoromethanesulfonic anhydride (7.4 mL). After stirring for about 6 minutes, the, 2-iso-propylanisole (1a; 10 g) is added in one portion. The reaction is kept in an room temperature water bath. The reaction stirs for about 16 hours and is then concentrated under reduced pressure. The material is taken up in 400 mL ethyl acetate. This is washed with 400 mL water, then 250 mL saturated sodium bicarbonate and finally 250 mL saturated NaCl solution. The organic layer is dried over sodium sulfate, filtered, and concentrated under reduced pressure. This material is recrystallized from heptane. The crystals are dissolved in 50 mL glacial acetic acid and placed in a 9° C. water bath and the reaction is stirred for 30 minutes. Peracetic acid, 32% in dilute acetic acid (29 mL) is added. The reaction is stirred in the water bath overnight, rising to room temperature. In the morning, the bath is changed to an ice water bath and the solution equilibrates for about 30 minutes. At this time, a sodium bisulfite solution (13.73 g in 48 mL water) is added dropwise. The reaction is stirred for 1 hour and poured into a separatory funnel. The aqueous layer is extracted with 250 mL hexanes. The organic layer is separated and the aqueous layer is extracted two more times with 100 mL hexanes. The organic layers are combined and back extracted with 3×100 mL water, once with 150 mL brine and is dried over sodium sulfate and concentrated under reduced pressure. The material is dissolved in methanol (68 mL) and stirred. The solution is cooled in an ice bath and 1N sodium hydroxide solution (68.4 mL) and is added dropwise. The ice bath is removed and the reaction is allowed to warm to room temperature and stir for 3 hours. The reaction is concentrated under reduced pressure and taken up in 250 mL ethyl acetate and extracted with 100 mL 1N NaOH twice, 100 mL water, and 100 mL brine. The solution is dried over sodium sulfate and concentrated under reduced pressure to afford 1j.

1k. 2-iso-propyl-4-(N,N-dimethylthiocabamoloxy)anisole: N,N-dimethylthiocarbamoyl chloride (10.9 g), 3-iso-propyl-4-methoxyphenol (1j; 10 g) and 1,4-diazabicyclo[2.2.2]octane (13.4 g) are combined in 250 mL DMF. The reaction is heated with stirring at 70° C. for one hour. At this time, the reaction is cooled to room temperature and filtered. The filtrate is concentrated under reduced pressure and the resulting solid is washed well with water and dried to afford 1k.

1l. 2-iso-propyl-4-(N,N-dimethylcabamoylthio)anisole: 2-iso-propyl-4-(N,N-dimethylthiocabamoyloxy) anisole, 6 g, is heated under a nitrogen atmosphere at 230° C. for one hour. At this time, the reaction is cooled to room temperature and the product is purified by chromatography on silica gel (hexane:ethyl acetate) to afford 1L.

1e. 3-iso-propyl-4-methoxythiophenol: 2-iso-propyl-4-(N,N-dimethylcabamoylthio)anisole (2 g) in 100 mL 10% aqueous sodium hydroxide and 10 mL ethanol is heated to reflux under nitrogen overnight. At this time, it is cooled and extracted once with ethyl acetate. The aqueous phase is acidified with 6 N HCl and then extracted twice with ethyl acetate. The organic layers are combined and washed with water and brine then dried over sodium sulfate and filtered. The filtrate is concentrated under reduced pressure and purified by chromatography on silica gel (hexane:ethyl acetate) to afford 1e.

Example 2

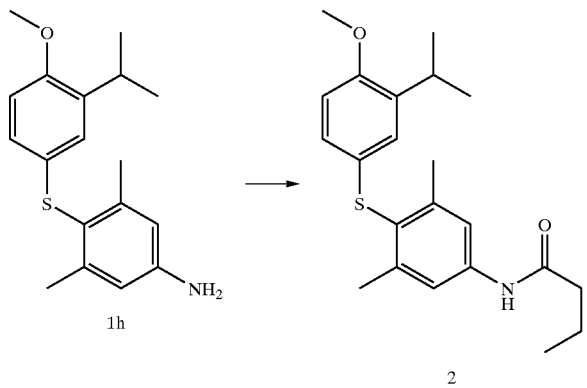

2. N-[3,5-dimethyl-4-(4'-methoxy-3'-iso-propylthiophenoxy)phenyl]butyramide: 2',6'-dimethyl-3-iso-propyl-4-methoxy-4'-aminodiphenylthioether (1h; 0.23 g) is suspended in pyridine, 0.12 mL, and butyric anhydride (0.23 mL) is added. The reaction is allowed to proceed for two hours and then it is concentrated under reduced pressure. The resulting residue is presorbed onto silica gel using acetone and purified by chromatography on silica gel (hexanes:ethyl acetate). The product is crystallized from hexanes to afford 2.

Example 3

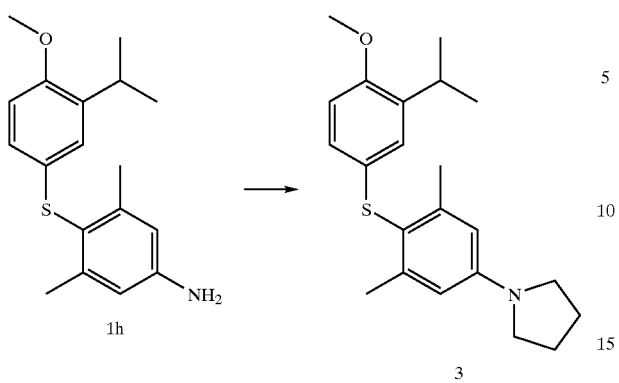

3. N-[3,5-dimethyl-4-(4'-methoxy-3'-iso-propylthiophenoxy)phenyl]pyrrolidine: 2',6'-dimethyl-3-iso-propyl-4-methoxy-4'-aminodiphenylthioether (1h; 1.58 g) is dissolved in 2 mL ethanol and 0.75 mL 1,4-diiodobutane is added. The sample is refluxed overnight. At this time, it is concentrated under reduced pressure. The sample is taken up in ethyl acetate and extracted with 0.1 N sodium hydroxide, water, and brine. After drying over sodium sulfate, filtering and concentration under reduced pressure, it is purified by chromatography on silica gel (hexane:ethyl acetate) to afford 3.

Example 4

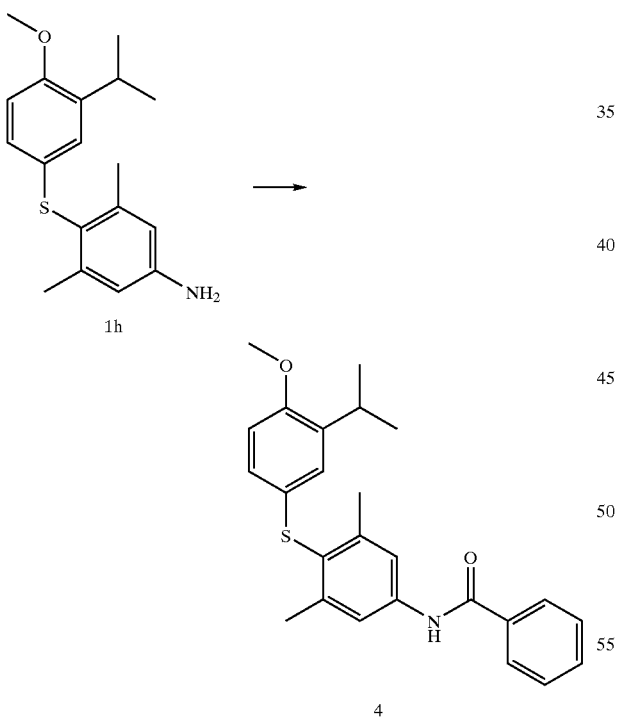

4. N-[3,5-dimethyl-4-(4'-methoxy-3'-iso-propylthiophenoxy)phenyl]benzamide: 2',6'-dimethyl-3-iso-propyl-4-methoxy-4'-aminodiphenylthioether (1h; 0.245 g) is suspended in pyridine (1 mL). To this solution is added 0.24 mL benzoyl chloride and the reaction is stirred 1 hour. The sample is concentrated under reduced pressure and dissolved in ethyl acetate. This is washed with water and brine then dried over magnesium sulfate and concentrated under reduced pressure. The residue is recrystallized from ethyl acetate:hexanes to afford 4.

Example 5

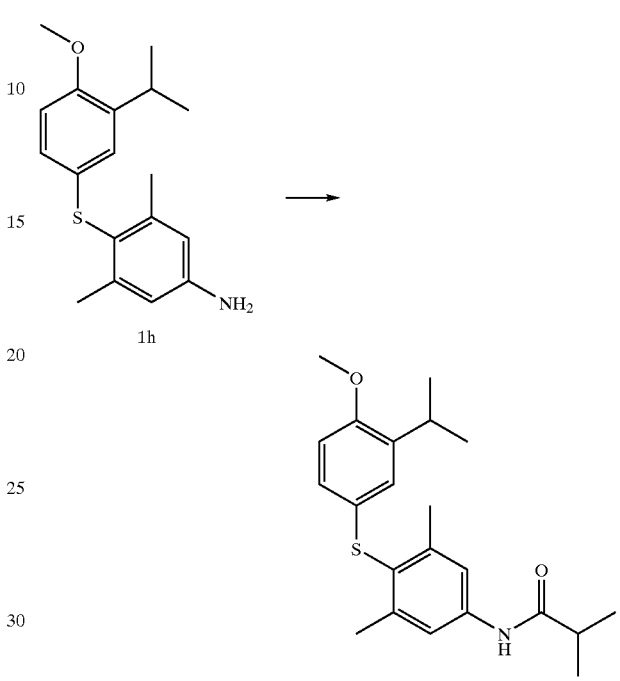

5. N-[3,5-dimethyl-4-(4'-methoxy-3'-iso-propylthiophenoxy)phenyl]-2-methylpropionamide: Isobutyric anhydride (4 mL) is added to 2',6'-dimethyl-3-iso-propyl-4-methoxy-4'-aminodiphenylthioether (1h; 0.225 g) and the reaction is stirred overnight. At this time, 20 mL water and 20 mL ethyl acetate are added and the reaction mixture is extracted with 1 N NaOH until the aqueous layer has a pH above 10. After extracting once with brine, drying over magnesium sulfate and filtering, the organic layer is concentrated under reduced pressure and purified by chromatography on silica gel (hexane:ethyl acetate) to afford 5.

Example 6

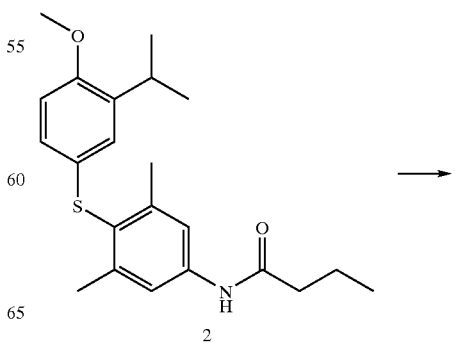

Example 7

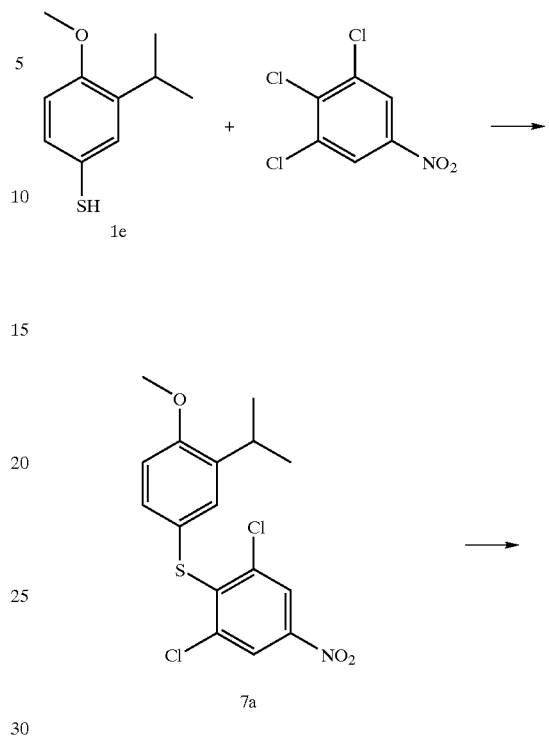

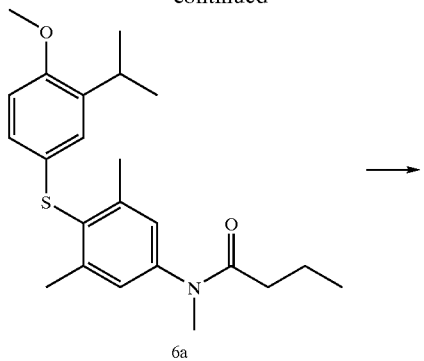

6a. N-methyl-N-[3,5-dimethyl-4-(4'-methoxy-3'-iso-propylthiophenoxy)phenyl]butyramide: In a dry flask under nitrogen, 0.32 g sodium hydride is suspended in 5 mL THF and stirred 10 minutes. To this solution is added dropwise N-(3,5-dimethyl-4-(4'-methoxy-3'-iso-propylthiophenoxy)phenyl)butyramide (2; 1 g) in 5 mL THF. The reaction is stirred for 15 minutes and methyl iodide (0.28 mL) is added dropwise. After 2 hours, the reaction is poured into ice water and extracted with chloroform. The organic layer is washed once with water, once with brine then dried over magnesium sulfate and concentrated under reduced pressure. The product is purified by chromatography on silica gel (hexanes:ethyl acetate) to afford 6a.

6b. N-methyl-N-[3,5-dimethyl-4-(4'-methoxy-3'-iso-propylthiophenoxy)phenyl]butylamine: In a dry flask under nitrogen is placed lithium aluminum hydride (1 g). To this is added 30 mL THF dropwise. After stirring 10 minutes, a solution of N-methyl-N-[3,5-dimethyl-4-(4'-methoxy-3'-iso-propylthiophenoxy)phenyl)butyramide (6a, 1.36 g) in 6 mL THF is added dropwise and the reaction is refluxed for about 16 hours. At this time, the reaction is cooled in an ice bath and 12 mL water is added dropwise followed by dropwise addition of 12 mL 15% sodium hydroxide, then 60 mL water. The reaction is stirred for 90 minutes. At this time, it is filtered through celite and washed with THF and ethyl acetate. The filtrate is concentrated under reduced pressure and the product is purified by chromatography on silica gel (hexane:ethyl acetate) to afford 6b.

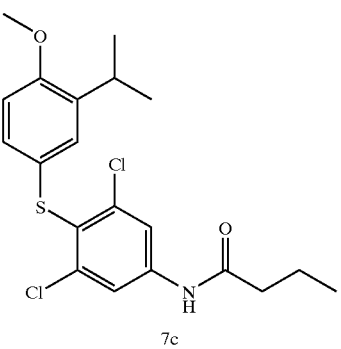

7a. 2',6'-dichloro-3-iso-propyl-4-methoxy-4'-nitrodiphenyl thioether: Potassium carbonate (6.8 g) is suspended in methylsulfoxide (100 mL). 1,2,3-trichloro-5-nitrobenzene (9.9 g) is added followed by 3-iso-propyl-4-methoxythiophenol (1e; 8 g). The reaction is heated to 37° C. and stirred under nitrogen with a mechanical stirrer for 20 hours. At this time, 200 mL cold water is added while stirring. After stirring for 2 hours the reaction mixture is filtered through a medium porosity frit and the filter cake is dried under reduced pressure to afford 7a.

7b. 3,5-dichloro-4-(4'-methoxy-3'-iso-propylthiophenoxy)benzylamine: 2',6'-dichloro-3-iso-propyl-4-methoxy-4'-nitrodiphenyl thioether (7a; 0.35 g) is dissolved in 5 mL of 49:1 ethanol:ethyl acetate by heating on a water bath (40° C.) and to this solution, tin chloride dihydrate (1 g) is added. The reaction is heated to 70° C. and stirred for about 1.5 hours. The reaction is allowed to cool to room temperature, then poured onto ice. The pH is made slightly basic (pH 7–8) by addition of 5% aqueous sodium bicarbonate (50 mL) and then extracted with ethyl acetate (50 mL). The organic phase is washed with brine (50 mL), treated with charcoal, dried over $MgSO_4$, and filtered. The filtrate is evaporated to provide 7b. Alternatively, 2',6'-dichloro-3-iso-propyl-4-methoxy-4'-nitrodiphenyl thioether (7a; 0.4 g) is dissolved in 15 mL 1:1 ethyl acetate:ethanol and 60 mg of 10% palladium on carbon is added. The reaction is hydrogenated, then filtered through Celite and concentrated under reduced pressure to afford 7b.

7c. N-[3,5-dichloro-4-(4'-methoxy-3'-iso-propylthiophenoxy)phenyl]butyramide: 3.5-dichloro-4-(4'-methoxy-3'-iso-propylthiophenoxy)benzylamine (7b, 0.22 g) is suspended in pyridine, 0.12 mL, and butyric anhydride (0.23 mL) is added. The reaction is allowed to proceed for two hours and then it is concentrated under reduced pressure. The resulting residue is presorbed onto silica gel using acetone and purified by chromatography on silica gel (hexanes:ethyl acetate) to afford 7c.

Example 8

8a. 3-tert-butyl-4-methoxythiophenol: 3-tert-butyl-4-methoxythiophenol (8a) is prepared analogously to the synthesis of 3-iso-propyl-4-methoxythiophenol (1e), which is described above, by substituting 2-tert-butyl phenol as a starting material for 2-iso-propyl phenol.

8b. 3,4-dichloro-5-methyl-nitrobenzene: 3,4-dichloro-5-methyl-nitrobenzene (8b) is prepared analogously to the synthesis of 4-chloro-3,5-dimethyl-nitrobenzene (1f), which is described above, by substituting 2-chloro-4-nitro-6-methylphenol for 2,6-dimethyl-4-nitrophenol.

8c. 3-chloro-5-methyl-4-(3'-tert-butyl-4'-methoxythiophenoxy)-nitrobenzene: 3,4-dichloro-5-methyl-nitrobenzene (8b; 195 mg) and 3-tert-butyl-4-methoxythiophenol (8a; 150 mg) are dissolved into 7.5 mL methylsulfoxide. To this solution, anhydrous potassium carbonate (150 mg) is added and the reaction mixed under nitrogen for 23 hours at 80° C. 50 mL ice water is added. The mixture is then extracted with 75 mL ethyl acetate. The organic layer is extracted once with 50 mL brine solution, dried with magnesium sulfate, and concentrated under high vacuum to afford 8c.

8d. 2'-chloro-6'-methyl-3-tert-butyl-4-methoxy-4'-aminodiphenylthioether: 2'-chloro-6'-methyl-3-tert-butyl-4-methoxy-4'-aminodiphenylthioether (8d) is prepared analogously to the synthesis of 3,5-dichloro-4-(4'-methoxy-3'-iso-propylthiophenoxy)benzylamine (7b), which is described above, by substituting 3-chloro-5-methyl-4-(3'-tert-butyl-4'-methoxythiophenoxy)-nitrobenzene (8c) for 2',6'-dichloro-3-iso-propyl-4-methoxy-4'-nitrodiphenyl thioether (7a).

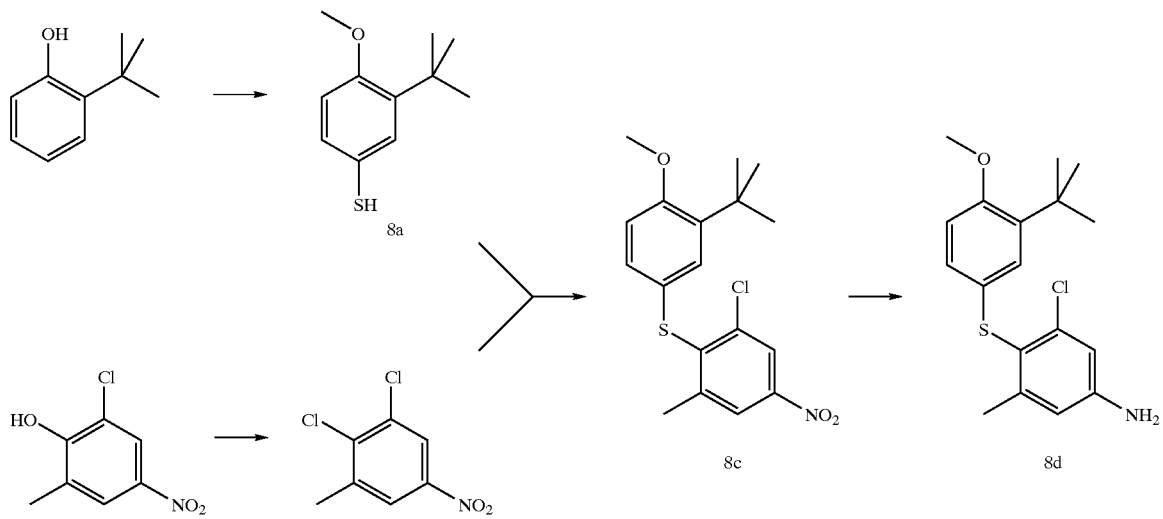

Example 9

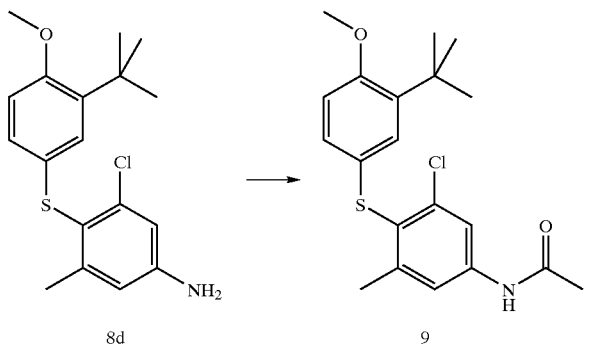

9. N-(3-chloro-5-methyl-4-(4'-methoxy-3'-tert-butylthiophenoxy)phenyl)acetamide: Acetic anhydride (4 mL) is added to 2'-chloro-6'-methyl-3-tert-butyl-4-methoxy-4'-aminodiphenylthioether (8d, 0.25 g) and the reaction is stirred overnight. At this time, 20 mL water and 20 mL ethyl acetate are added and the reaction mixture is extracted with 1 N NaOH until the aqueous layer has a pH above 10. After extracting once with brine, drying over magnesium sulfate and filtering, the organic layer is concentrated under reduced pressure and purified by chromatography on silica gel (hexane:ethyl acetate) to afford 9.

Example 10

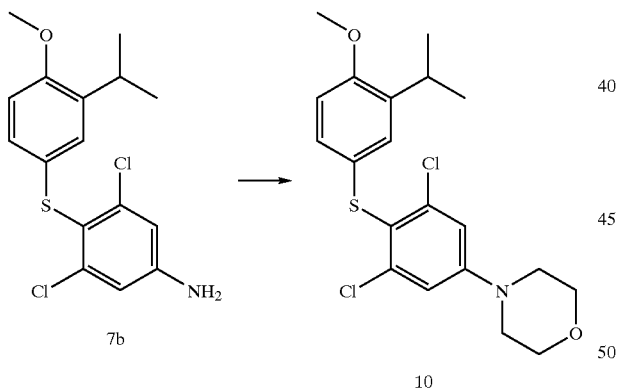

10. N-[3,5-dichloro-4-(4'-methoxy-3'-iso-propylthiophenoxy)phenyl]morpholine: 3,5-dichloro-4-(4'-methoxy-3'-iso-propylthiophenoxy)benzylamine (7b; 0.25 g) is dissolved in 2 mL ethanol and 0.15 g di(2-iodoethyl)ether is added. The sample is refluxed overnight. At this time, it is concentrated under reduced pressure. The sample is taken up in ethyl acetate and extracted with 0.1 N sodium hydroxide, then water and brine. After drying over sodium sulfate, filtering, and concentrating the filtrate under reduced pressure, it is purified by chromatography on silica gel (hexanes:ethyl acetate) to afford 10.

Example 11

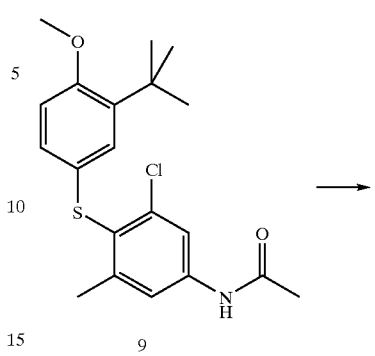

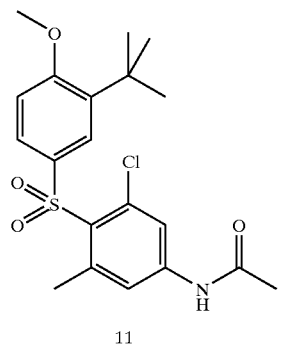

11. N-[3-chloro-5-methyl-4-(4'-methoxy-3'-tert-butylphenylsulfonyl)phenyl]acetamide: N-[3-chloro-5-methyl-4-(4-methoxy-3-tert-butylthiophenoxy)phenyl]acetamide (9; 0.5 g) and 50% 3-chloroperoxybenzoic acid (1 g) in dichloromethane is stirred for 20 hours. At this time, the reaction is treated with aqueous sodium bisulfite to quench excess peracid, then the organic layer is isolated and washed with saturated sodium carbonate, water, brine and dried over sodium sulfate. The solution is filtered, the filtrate is concentrated under reduced pressure, and the product is purified by chromatography on silica gel (hexanes:ethyl acetate) to afford 11.

Example 12

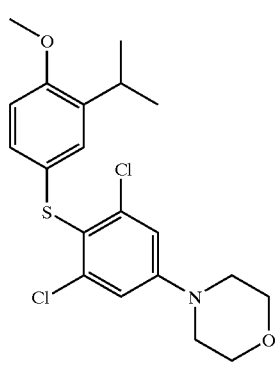

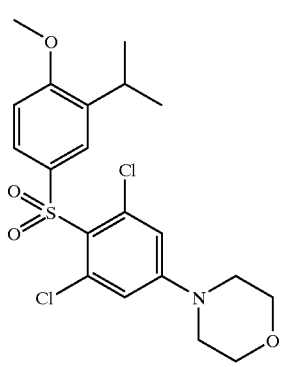

12

12. N-[3,5-dichloro-4-(4'-methoxy-3'-iso-propylphenylsulfonyl)phenyl]morpholine: N-[3,5-dichloro-4-(4'-methoxy-3'-iso-propylthiophenoxy)phenyl]morpholine (10; 0.25 g) and 50% 3-chloroperoxybenzoic acid (0.46 g) in dichloromethane is stirred for 20 hours. At this time, the reaction is treated with aqueous sodium bisulfite to quench excess peracid, then the organic layer is isolated and washed with saturated sodium carbonate, water, brine and dried over sodium sulfate. The solution is filtered, the filtrate is concentrated under reduced pressure, and the product is purified by chromatography on silica gel (hexanes:ethyl acetate) to afford 12.

Example 13

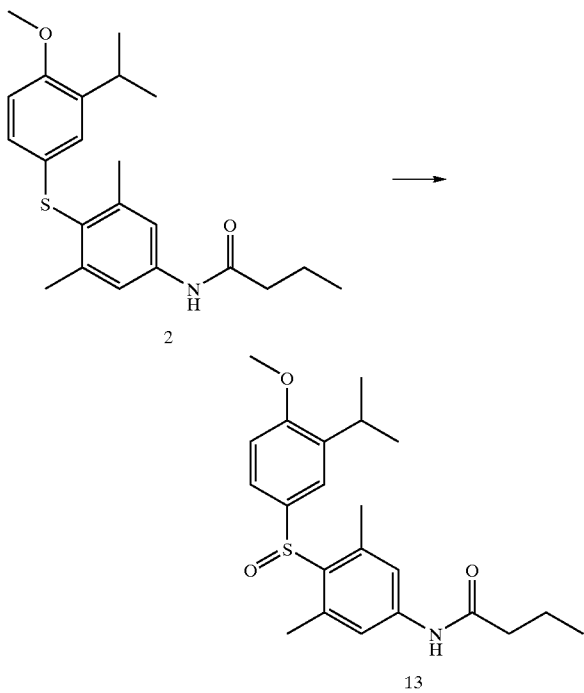

13. N-[3,5-dimethyl-4-(4'-methoxy-3'-iso-propylphenylsulfonyl)phenyl]butyramide: A mixture of N-[3,5-dimethyl-4-(4'-methoxy-3'-iso-propylthiophenoxy)phenyl]butyramide (2; 1.1 g), 1.2 mL 5M tert-butylhydroperoxide in nonane, and 70 mg camphor sulphonic acid are taken up in 15 mL dichloromethane and stirred for 20 hours. At this time, the reaction mixture is poured directly onto a silica gel column and the product is isolated by chromatography with hexanes:ethyl acetate.

Use of the Present Compounds

According to the methods of the present invention, a compound having a structure as described herein is administered, most preferably with a pharmaceutically-acceptable or cosmetically-acceptable carrier.

The compounds of the present invention may be used for the treatment of such conditions as treating hair loss in mammals, including arresting and / or reversing hair loss and promoting hair growth. Such conditions may manifest themselves in, for example, alopecia, including male pattern baldness and female pattern baldness.

In addition, the compounds of the present invention may be useful for weight control, including the treatment and/or prevention of obesity. Other uses for the compounds of the present invention include stimulation of nail growth, treatment of skin conditions, prevention of hair discoloration, obesity, cholesterol lowering, treatment of thyroid disorders, and treatment of osteoporosis.

Preferably the compounds of the present invention are, as, defined herein, cardiac-sparing.

Preferably, the compounds are formulated into pharmaceutical or cosmetic compositions for use in treatment or prophylaxis of conditions such as the foregoing. Standard pharmaceutical formulation techniques are used, such as those disclosed in *Remington's Pharmaceutical Sciences*, Mack Publishing Company, Easton, Pa. (1990).

Typically, from about 5 mg to about 3000 mg, more preferably from about 5 mg to about 1000 mg, more preferably from about 10 mg to about 100 mg, of a compound having a structure as described herein is administered per day for systemic administration. It is understood that these dosage ranges are by way of example only, and that daily administration can be adjusted depending on various factors. The specific dosage of the compound to be administered, as well as the duration of treatment, and whether the treatment is topical or systemic are interdependent. The dosage and treatment regimen will also depend upon such factors as the specific compound used, the treatment indication, the efficacy of the compound, the personal attributes of the subject (such as, for example, weight, age, sex, and medical condition of the subject), compliance with the treatment regimen, and the presence and severity of any side effects of the treatment.

According to the present invention, the subject compounds are co-administered with a pharmaceutically-acceptable or cosmetically-acceptable carrier (herein collectively described as carrier'). The term "carrier", as used herein, means one or more compatible solid or liquid filler diluents or encapsulating substances which are suitable for administration to a mammal. The term "compatible", as used herein, means that the components of the composition are capable of being commingled with a compound of the present invention, and with each other, in a manner such that there is no interaction which would substantially reduce the efficacy of the composition under ordinary use situations. Carriers must, of course, be of sufficiently high purity and sufficiently low toxicity to render them suitable for administration to the animal, preferably mammal (most preferably human), being treated. The carrier can itself be inert or it can possess pharmaceutical and/or cosmetic benefits of its own.

The compositions of this invention may be in any of a variety of forms, suitable (for example) for oral, rectal, topical, nasal, ocular or parenteral administration. Of these, topical and/or oral administration are especially preferred with topical being most preferred. Depending upon the particular route of administration desired, a variety of carriers well-known in the art may be used. These include solid or liquid fillers, diluents, hydrotropes, surface-active agents, and encapsulating substances. Optional pharmaceutically-active or cosmetically-active materials may be included which do not substantially interfere with the activity of the compound of the present invention. The amount of carrier employed in conjunction with the compound is sufficient to provide a practical quantity of material for administration per unit dose of the compound. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Some examples of substances which can serve as carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a carrier to be used in conjunction with the subject compound is typically determined by the way the compound is to be administered.

In particular, carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the carrier, in compositions for parenteral administration, comprises at least about 90% by weight of the total composition.

Various oral dosage forms can be used, including such solid forms as tablets, capsules, granules and bulk powders. These oral forms comprise a safe and effective amount, usually at least about 5%, and preferably from about 25% to about 50%, of a compound used in the present invention. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The carriers suitable for the preparation of unit dosage forms for oral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components depends on secondary considerations like taste, cost, and shelf stability, which are not critical for the purposes of the subject invention, and can be readily made by a person ordinarily skilled in the art.

Orally administered compositions also include liquid solutions, emulsions, suspensions, powders, granules, elixirs, tinctures, syrups, and the like. The carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compounds of the present invention may also be topically administered. The carrier of the topical composition preferably aids penetration of the present compounds into the skin to reach the environment of the hair follicle. Topical compositions of the present invention may be in any form including, for example, solutions, oils, creams, ointments, gels, lotions, shampoos, leave-on and rinse-out hair conditioners, milks, cleansers, moisturizers, sprays, skin patches, and the like.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, iso-propyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, iso-propyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, methylsulfoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, tri-alkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compounds used in the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines. A preferred formulation for topical delivery of the present compounds utilizes liposomes such as described in Dowton et al., "Influence of Liposomal Composition on Topical Delivery of Encapsulated Cyclosporin A: I. An in vitro Study Using Hairless Mouse Skin", S.T.P. Pharma Sciences, Vol. 3, pp. 404–407 (1993); Wallach and Philippot, "New Type of Lipid Vesicle: Novasome®", Liposome Technology, Vol. 1, pp. 141–156 (1993); Wallach, U.S. Pat. No. 4,911,928, assigned to Micro-Pak, Inc., issued Mar. 27, 1990; and Weiner et al., U.S. Pat. No. 5,834,014, assigned to The University of Michigan and Micro-Pak, Inc., issued Nov. 10, 1998 (with respect to Weiner et al., with a compound as described herein administered in lieu of, or in addition to, minoxidil).

The compounds of the present invention may also be administered by iontophoresis. See, e.g., internet site www.unipr.it/arpa/dipfarm/erasmus/erasm14.html; Banga et al., "Hydrogel-based Iontotherapeutic Delivery Devices for Transdermal Delivery of Peptide/Protein Drugs", Pharm. Res., Vol. 10 (5), pp. 697–702 (1993); Ferry, "Theoretical Model of Iontophoresis Utilized in Transdermal Drug Delivery", Pharmaceutical Acta Helvetiae, Vol 70, pp. 279–287 (1995); Gangarosa et al., "Modern Iontophoresis for Local Drug Delivery", Int. J. Pharm, Vol. 123, pp. 159–171 (1995); Green et al., "Iontophoretic Delivery of a Series of Tripeptides Across the Skin in vitro", Pharm. Res., Vol 8, pp. 1121–1127 (1991); Jadoul et al., "Quantification and Localization of Fentanyl and TRH Delivered by Iontophoresis in the Skin", Int. J. Pharm., Vol. 120, pp. 221–8 (1995); O'Brien et al., "An Updated Review of its Antiviral Activity, Pharmacokinetic Properties and Therapeutic Efficacy", Drugs, Vol. 37, pp. 233–309 (1989); Parry et al., "Acyclovir Bioavailability in Human Skin", J. Invest. Dermatol., Vol. 98 (6), pp. 856–63 (1992); Santi et al., "Drug Reservoir Composition and Transport of Salmon Calcitonin in Transdermal Iontophoresis", Pharm. Res., Vol 14 (1), pp. 63–66 (1997); Santi et al., "Reverse Iontophoresis-Parameters Determining Electroosmotic Flow: I. pH and Ionic Strength", J. Contuol. Release, Vol. 38, pp. 159–165 (1996); Santi et al., "Reverse Iontophoresis—Parameters Determining Electroosmotic Flow: II. Electrode Chamber Formulation", J. Control. Release, Vol. 42, pp. 29–36 (1996); Rao et al., "Reverse Iontophoresis: Noninvasive Glucose Monitoring in vivo in Humans", Pharm. Res., Vol. 12 (12), pp. 1869–1873 (1995); Thysman et al., "Human Calcitonin Delivery in Rats by Iontophoresis", J. Pharm. Pharmacol., Vol. 46, pp. 725–730 (1994); and Volpato et al., "Iontophoresis Enhances the Transport of Acyclovir through Nude Mouse Skin by Electrorepulsion and Electroosmosis", Pharm. Res., Vol. 12 (11), pp. 1623–1627 (1995).

The compositions used in the present invention may also optionally comprise an activity enhancer. The activity enhancer can be chosen from a wide variety of molecules which can function in different ways to enhance hair growth effects of a compound of the present invention. Particular classes of activity enhancers include other hair growth stimulants and penetration enhancers.

Non-limiting examples of other hair growth stimulants which may be used in the compositions herein, including both systemic and topical compositions, include, for example, benzalkonium chloride, benzethonium chloride, phenol, estradiol, diphenhydramine hydrochloride, chlorpheniramine maleate, chlorophyllin derivatives, cholesterol, salicylic acid, cysteine, methionine, red pepper tincture, benzyl nicotinate, D,L-menthol, peppermint oil, calcium pantothenate, panthenol, castor oil, hinokitiol, prednisolone, resorcinol, monosaccharides and esterified monosaccharides, chemical activators of protein kinase C enzymes, glycosaminoglycan chain cellular uptake inhibitors, inhibitors of glycosidase activity, glycosaminoglycanase inhibitors, esters of pyroglutamic acid, hexosaccharic acids or acylated hexosaccharic acids, aryl-substituted ethylenes, N-acylated amino acids, and, of course, minoxidil or finasteride. The most preferred activity enhancers are minoxidil and finasteride, most preferably minoxidil.

Non-limiting examples of penetration enhancers which may be used in the compositions herein include, for example, 2-methyl propan-2-ol, propan-2-ol, ethyl-2-hydroxypropanoate, hexan-2,5-diol, POE(2) ethyl ether, di(2-hydroxypropyl) ether, pentan-2,4-diol, acetone, POE(2) methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, POE ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, iso-propyl palmitate, ethyl laurate, 2-ethyl-hexyl pelargonate, iso-propyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hyroxyoctanoic acid, methylsulfoxide, N,N-dimethyl acetamide, N,N-dimethyl formamide, 2-pyrrolidone, 1-methyl-2-pyrrolidone, 5-methyl-2-pyrrolidone, 1,5- dimethyl-2-pyrrolidone, 1-ethyl-2-pyrrolidone, phosphine oxides, sugar esters, tetrahydrofurfural alcohol, urea, diethyl-m-toluamide, and, 1-dodecylazacyloheptan-2-one.

In all of the foregoing, of course, the compounds used in the present methods can be administered alone or as mixtures, and the compositions may further include additional drugs or excipients as appropriate for the indication.

The present invention further relates to kits comprising a compound and/or composition of the present invention and information and/or instructions by words, pictures, and/or the like, that use of the kit will provide treatment for hair loss in mammals (particularly humans) including, for example, arresting and/or reversing hair loss and/or promoting hair growth. In addition or in the alternative, the kit may comprise a compound and/or composition of the present invention and information and/or instructions regarding methods of application of the compound and/or composition, preferably with the benefit of treating hair loss in mammals.

EXAMPLES OF COMPOSITION ADMINISTRATION

The following examples do not limit the invention, but provide guidance to the ordinarily skilled artisan to perform the methods of the present invention. In each example, a compound other than the one mentioned may be substituted in the example by another having a structure as described herein with similar results.

Example A

A composition for topical administration is made, comprising:

| Component | Amount |
| --- | --- |
| Compound of Example 3 | 5% |
| Ethanol | 57% |
| Propylene Glycol | 19% |
| Dimethyl Isosorbide | 19% |

A human male subject suffering from male pattern baldness is treated by a method of this invention. Specifically, for 6 weeks, the above composition is daily administered topically to the subject.

Example B

A composition for topical administration is made according to the method of Dowton et al., "Influence of Liposomal Composition on Topical Delivery of Encapsulated Cyclosporin A: I. An in vitro Study Using Hairless Mouse Skin", *S.T.P. Pharma Sciences*, Vol. 3, pp. 404–407 (1993), using the compound of Example 2 in lieu of cyclosporin A and using the Novasome 1 for the non-ionic liposomal formulation.

A human male subject suffering from male pattern baldness is treated each day with the above composition. Specifically, for 6 weeks, the above composition is administered topically to the subject.

Example C

A shampoo is made, comprising:

| Component | Ex. C-1 | Ex. C-2 | Ex. C-3 | Ex. C-4 |
| --- | --- | --- | --- | --- |
| Ammonium Lauryl Sulfate | 11.5% | 11.5% | 9.5% | 7.5% |
| Ammonium Laureth Sulfate | 4% | 3% | 2% | 2% |
| Cocamide MEA | 2% | 2% | 2% | 2% |
| Ethylene Glycol Distearate | 2% | 2% | 2% | 2% |
| Cetyl Alcohol | 2% | 2% | 2% | 2% |
| Stearyl Alcohol | 1.2% | 1.2% | 1.2% | 1.2% |
| Glycerin | 1% | 1% | 1% | 1% |
| Polyquaternium 10 | 0.5% | 0.25% | — | — |
| Polyquaternium 24 | — | — | 0.5% | 0.25% |
| Sodium Chloride | 0.1% | 0.1% | 0.1% | 0.1% |
| Sucrose Polyesters of Cottonate Fatty Acid | 3% | 3% | — | — |
| Sucrose Polyesters of Behenate Fatty Acid | 2% | 3% | — | — |
| Polydimethyl Siloxane | — | — | 3% | 2% |
| Cocaminopropyl Betaine | — | 1% | 3% | 3% |
| Lauryl Dimethyl Amine Oxide | 1.5% | 1.5% | 1.5% | 1.5% |
| Decyl Polyglucose | — | — | 1% | 1% |
| DMDM Hydantoin | 0.15% | 0.15% | 0.15% | 0.15% |
| Compound of Example 1 | — | 3% | 3% | — |
| Compound of Example 4 | 6% | — | — | 6% |
| Minoxidil | — | — | 3% | 2% |
| Phenoxyethanol | 0.5% | 0.5% | 0.5% | 0.5% |
| Fragrance | 0.5% | 0.5% | 0.5% | 0.5% |
| Water | q.s. | q.s. | q.s | q.s |

A human subject suffering from male pattern baldness is treated by a method of this invention. Specifically, for 12 weeks, the above shampoo is used daily by the subject.

What is claimed is:

1. A compound characterized by the structure:

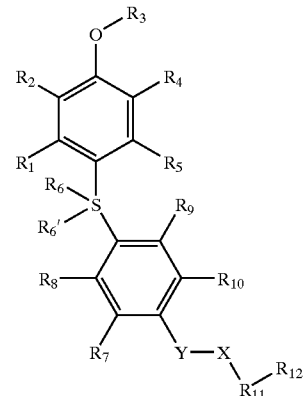

and pharmaceutically acceptable salts, hydrates wherein:
$R_1$, $R_2$, $R_5$, $R_7$, and $R_{10}$ are each, independently, selected from the group consisting of hydrogen, halogen, alkyl, alkenyl, alkynyl, heteroalkyl, heteroalkenyl, and heteroalkynyl;

$R_4$ is selected from the group consisting of halogen, alkyl, alkenyl, alkynyl, cycloalkyl, cycloalkenyl, aryl, arylalkyl, heteroalkyl, heteroalkenyl, heteroalkynyl, heterocycloalkyl, heterocycloalkenyl, heteroaryl, heteroarylalkyl, and heteroarylalkenyl;

$R_8$ and $R_9$ are each, independently, selected from the group consisting of halogen, alkyl, alkenyl, alkynyl, cycloalkyl, cycloalkenyl, aryl, arylalkyl, heteroalkyl, heteroalkenyl, heteroalkynyl, heterocycloalkyl, heterocycloalkenyl, heteroaryl, heteroarylalkyl, and heteroarylalkenyl;

$R_3$ is selected from the group consisting of hydrogen, alkyl, alkenyl, alkynyl, cycloalkyl, cycloalkenyl, aryl, arylalkyl, heteroalkyl, heteroalkenyl, heteroalkynyl, heterocycloalkyl, heterocycloalkenyl, heteroaryl, heteroarylalkyl and heteroarylalkenyl;

$R_6$ and $R_6'$ are each, independently, selected from the group consisting of nil and oxo;

Y is bond;

X is selected from the group consisting of —NZ— and —NH—;

$R_{11}$ is selected from the group consisting of bond and —C(O)—;

$R_{12}$ is selected from the group consisting of alkyl, alkenyl, alkynyl, heteroalkyl, heteroalkenyl, heteroalkynyl, cycloalkyl, cycloalkenyl, heterocycloalkyl, heterocycloalkenyl, aryl, arylalkyl, heteroaryl, heteroarylalkyl, and heteroarylalkenyl; with the provisos that when $R_{11}$ is bond, then $R_{12}$ and Z optionally are bonded together to form a cycle selected from the group consisting of a morpholine and a pyrrolidine; when $R_{12}$ is heteroalkyl, heteroalkenyl, heteroalkynyl, heterocycloalkyl, heterocycloalkenyl, heteroaryl, heteroarylalkyl, or heteroarylalkenyl, then a heteroatom of $R_{12}$ is not directly covalently bonded to $R_{11}$; when $R_{12}$ is heteroalkyl, heteroalkenyl, heteroalkynyl, heterocycloalkyl, heterocycloalkenyl, heteroaryl, heteroarylalkyl, or heteroarylalkenyl, then a heteroatom of $R_{12}$ is not directly covalently bonded to $R_{11}$; and Z is selected from the group consisting of alkyl, alkenyl, alkynyl, heteroalkyl, heteroalkenyl, and heteroalkynyl; with the proviso that when $R_{11}$ is bond, then $R_{12}$ and Z are optionally bonded together to form a cycle selected from the group consisting of a morpholine and a pyrrolidine; wherein when $R_{12}$ is heteroalkyl, heteroalkenyl, heteroalkynyl, heterocycloalkyl, heterocycloalkenyl, heteroaryl, heteroarylalkyl, or heteroarylalkenyl, then a heteroatom of $R_{12}$ is not directly covalently bonded to $R_{11}$.

2. A compound according to claim 1 wherein $R_4$, $R_8$, and $R_9$ are each, independently, selected from the group consisting of halogen, alkyl, alkenyl, and heteroalkyl; with the proviso that $R_3$ is selected from the group consisting of hydrogen, lower alkyl, and lower alkenyl.

3. A compound according to claim 1 wherein $R_6$ and $R_6'$ are each nil.

4. A compound according to claim 3 wherein $R_{12}$ is selected from alkyl, heteroalkyl, arylalkyl, and heteroarylalkyl; with the proviso that when $R_{11}$ is bond, then $R_{12}$ and Z are optionally bonded together to form a cycle selected from the group consisting of a morpholine and a pyrrolidine.

5. A compound according to claim 1 wherein $R_1$, $R_2$, $R_5$, $R_7$, and $R_{10}$ are each hydrogen.

6. A composition comprising a compound of claim 1 and a carrier.

7. A method of treating hair loss comprising administering to a mammal a composition according to claim 6.

8. A method according to claim 7, wherein the administration is topical.

* * * * *